(12) United States Patent
Aldridge et al.

(10) Patent No.: US 7,378,104 B2
(45) Date of Patent: May 27, 2008

(54) DELIVERING SUBSTANCES TO INVERTEBRATE ORGANISMS

(75) Inventors: David Aldridge, Cambridge (GB); Geoffrey Dillwyn Moggridge, Cambridge (GB)

(73) Assignee: BioBullets Limited, London (GB)

( * ) Notice: Subject to any disclaimer, the term of this patent is extended or adjusted under 35 U.S.C. 154(b) by 0 days.

(21) Appl. No.: 10/181,552

(22) PCT Filed: Jan. 19, 2001

(86) PCT No.: PCT/GB01/00178

§ 371 (c)(1), (2), (4) Date: Jul. 19, 2002

(87) PCT Pub. No.: WO01/52634

PCT Pub. Date: Jul. 26, 2001

(65) Prior Publication Data

US 2003/0140863 A1    Jul. 31, 2003

(30) Foreign Application Priority Data

Jan. 21, 2000   (GB)   ................. 0001281.5

(51) Int. Cl.
    *A01N 25/28*   (2006.01)
(52) U.S. Cl. .......... 424/410; 424/84; 424/408; 424/417; 424/640; 424/679; 424/777; 514/25
(58) Field of Classification Search .......... 119/212, 119/234, 235, 242, 51.04; 43/124, 131; 424/408, 424/417

See application file for complete search history.

(56) References Cited

U.S. PATENT DOCUMENTS

| 3,592,168 | A | | 7/1971 | Claus |
| 4,753,799 | A | * | 6/1988 | Nelsen et al. ............... 424/408 |
| 5,052,340 | A | | 10/1991 | Smucker et al. |
| 5,252,330 | A | | 10/1993 | Lee et al. |
| 5,273,749 | A | * | 12/1993 | Bok et al. ................... 424/405 |
| 5,334,386 | A | * | 8/1994 | Lee et al. ................... 424/777 |
| 5,375,626 | A | | 12/1994 | Fears |
| 5,503,836 | A | * | 4/1996 | Fellers et al. ............... 424/405 |

(Continued)

FOREIGN PATENT DOCUMENTS

CA   2290205   * 11/1999

(Continued)

OTHER PUBLICATIONS

S.W. Fisher et al., Molluscicidal Activity of Potassium to the Zebra Mussel Dreissena-Polymorpha Toxicity and Mode of Action Aquatic Toxicology, vol. 20, No. 4, 1991, pp. 219-234.*

(Continued)

*Primary Examiner*—Neil S. Levy
(74) *Attorney, Agent, or Firm*—Venable LLP; Marina V. Schneller

(57) ABSTRACT

Particles (10) for controlling, treating, feeding of aquatic invertebrate filter feeding organisms such as mussels, clams, oysters and insect larvae comprising a biologically active ingredient (13) embedded within or surrounded by an innocuous carrier material (12). The organism effectively concentrates the active ingredient within its body by feeding on the particles, thereby reducing the total amount of active ingredient required to be used.

26 Claims, 15 Drawing Sheets

U.S. PATENT DOCUMENTS

| | | | | |
|---|---|---|---|---|
| 5,510,110 | A | * | 4/1996 | Puritch et al. ............... 424/421 |
| 5,631,024 | A | * | 5/1997 | Kevan et al. ................ 424/486 |
| 5,698,191 | A | * | 12/1997 | Wiersma et al. ......... 424/78.09 |
| 5,972,363 | A | * | 10/1999 | Clikeman et al. ........... 424/408 |
| 6,410,622 | B1 | * | 6/2002 | Endres ....................... 524/189 |

FOREIGN PATENT DOCUMENTS

| | | | |
|---|---|---|---|
| CA | 2 290205 | | 8/2000 |
| JP | 07-242507 | | 9/1995 |
| WO | WO 97/41742 | * | 11/1997 |
| WO | WO 9741742 | | 11/1997 |

OTHER PUBLICATIONS

J.D. Shields et al., "Microencapsulation as a potential control technique against sabeillid worms in abalone culture", Journal of Shellfish Research, vol. 17, No. 1, Jun. 1998, pp. 79-83.

E.H. Ten Winkel et al., "Food selection by Dreissena polymorpha Pallas (Mollusca: Bivalvia)", Freshwat. Biol., vol. 12, No. 6, 1982, pp. 553-558.

S.W. Fisher et al., "Molluscicidal Activity of Potassium to the Zebra Mussel Dreissena-Polymorpha Toxicity and Mode of Action," Aquatic Toxicology, vol. 20, No. 4, 1991, pp. 219-234.

A. Lemma et al.; "Endod is Lethal to Zebra Mussels and Inhibits Their Attachment," Journal of Shellfish Research, vol. 10, No. 2, 1991, pp. 361-366.

P.A. Gabbott et al., "Studies on the design and acceptability of microencapsulated diets for marine particle feeders, II. Bivalve molluscs," Oroc. Eur. Symp. Mar. Biol., 10$^{th}$ (1976), Meeting Date 1975, vol. 1, 1976, pp. 127-141.

Aldridge, David C. et al., "Microencapsulated BioBullets for the Control of Biofouling Zebra Mussels", Environmental Science & Technology, 2006, vol. 40, No. 3, pp. 975-979.

* cited by examiner

★ indicates no mussels died under these conditions
★ᵃ indicates a single mussel died under these conditions

DELIVERING SUBSTANCES TO INVERTEBRATE ORGANISMS

The present invention relates to a composition and method for use in the delivery of a desired substance to invertebrate organisms. The invention is particularly applicable, but not restricted to, aquatic filter feeders such as bivalve molluscs (for example, mussels and clams) and insect larvae and may be used to deliver any desired substance having biological activity in the organism concerned, for example one or more toxic agents, growth promoters, nutrients, anti-parasitic agents, growth controllers, or reproduction promoters/inhibitors.

The present invention is concerned with the manipulation of any aspect of an invertebrate's physiology, growth, reproduction, resistance or vulnerability to disease or parasitic infestation or behaviour, including killing invasive invertebrate organisms by delivering an effective amount of a toxic agent thereto. "Manipulation" is to be interpreted also as restoring normal function and/or growth in an environment which would otherwise not support normal function and/or growth, for example a nutrient depleted environment.

Toxic agents may be used which have the effect of killing, weakening, debilitating or indeed inducing any effect which enables the pest to be displaced or more easily removed from the area or environment being controlled.

Conventionally, it is known to address the problem of infestations of bivalve mussels which adhere by means of their byssus threads or "beards" to hard substrates, such as power station cooling water intakes and associated auxiliary equipment, by injecting an aqueous solution of toxin into the water stream. Suitable toxins include chlorine-based agents such as sodium hypochlorite at a concentration of approximately 3 ppm.

It has been known for some time that simply putting the desired substance, for example a toxin, into the water in which bivalve molluscs, particularly mussels, are feeding can cause the mussels to close their shells and cease feeding, whereupon the substance has to be continually added to the water for about three weeks until the mussels are forced to resume feeding. This means that there is a considerable and undesirable amount of water pollution by the toxin.

Various attempts have been made to find a more environmentally acceptable way of delivering a substance such as a toxin to bivalve molluscs. For example, in U.S. Pat. No 5,252,330 to The University of Toledo, Zebra mussels (*Dreissena polymorpha*) are controlled by contacting the mussels with effective lethal amounts of an aqueous chemical treating medium comprising molluscicidally effective portions of the berry from *Phytolacca dodecandra* (also known as Endod) which contains a toxin ("Lemmatoxin") having the structural formula disclosed in British Patent No 1,227,417. When used as a treating agent in water, the Phytolacca treatment is preferably incubated to increase its chemical activity.

However, even such a plant-based and biodegradable toxin can cause considerable environmental damage and will kill organisms other than the target organism.

Accordingly it is one of the aims of the present invention to address problems with known compositions and methods of delivering substances to invertebrate organisms, whether referred to herein or otherwise.

The Applicants have surprisingly found that one or more desired substances may be targeted to the intended organisms (particularly mussels and clams) more efficiently if the organisms can be induced to continue ingesting the substance, thereby allowing a smaller total quantity of the substance to be used to achieve the desired effect, thereby minimising the environmental impact of the substance.

According to a first aspect of the present invention there is provided particles for ingestion by an invertebrate organism, said particles including at least one ingredient having desired biological activity in the organism when ingested by the organism and at least one carrier material, characterised in that the active ingredient is solid, toxic to the organism, and coated with or encapsulated within a water soluble carrier material.

Conveniently the above ingredient is embedded throughout the carrier material, or alternatively the active ingredient may be coated with or encapsulated within (for example by known microencapsulation techniques) the carrier material.

Preferably the organism is an aquatic invertebrate organism, for example a filter feeder such as a bivalve mollusc. Examples of bivalve molluscs to which the invention may be applied include mussels, particularly Zebra mussels, clams, particularly the Asian clam (Corbicula Fluminea), and oysters. Examples of other aquatic invertebrates to which the invention may be applied include insect larvae such as blackfly larvae. In tropical Africa the blackfly *Simulin damnosum* is the vector of onchoceriasis (river blindness) as well as reducing yields in cattle populations due to the blood-sucking habit of the adult flies which prevents efficient foraging. The only current method of blackfly control is to treat the water with DDT (dichlorodiphenyltrichloroethane) which presents major environmental risks.

By "biological activity" is meant any effect, or combination of effects, on any aspect of the organism's physiology, growth, reproduction, disease or parasite resistance or vulnerability, or behaviour, and includes causing or hastening the death of the organism either directly or indirectly. An ingredient having such biological activity in the organism will hereinafter be referred to as "the active ingredient" and includes substances, such as nutrients, which restore normal function and/or growth, in an environment which would otherwise inhibit or restrict said normal function and/or growth, for example due to insufficient, or complete lack of, essential nutrients.

Particularly, it is preferred that the effect is a physiological effect.

To render the particles ingestible, firstly the particle size is chosen to be suitable for ingestion by the target organism. For example, for bivalve molluscs such as mussels the mean particle size is preferably in the region of 1 to 200 microns or more in diameter, more preferably between 2 to 150 microns in diameter.

Zebra mussels are filter feeders, filtering around 1 gallon of water a day and selecting for ingestion particles up to 200 microns in diameter. The filtering structures are the large fleshy gills that lie on each side of the body, within the mantle cavity and these gills are covered by different types of cilia. The frontal cilia on the outer gill face beat towards the marginal groove which runs along the ventral free edge of the gill —coarse particles in excess of 200 microns pass down the crests of the gill surface and are excluded from the marginal groove, whereas smaller particles are directed along the groove and arrive at the labial palps. A proportion of the particles arriving at the labial palps are passed into the mouth.

For example, by providing the active ingredient in the form of particles which are compatible with this selective feeding mechanism and which are not detected by the organism as being toxic, the active ingredient is more effectively taken up by and will be concentrated in the target organism.

Preferably, the carrier material is not only innocuous for the target organism but is preferably also nutritious for and/or attractive to the target organism, thereby enhancing the ingestion of the particles.

In the preferred embodiment, the active ingredient is provided as a core surrounded by a coating of innocuous and/or nutritious and/or attractive carrier material around said core.

Alternatively, the treatment medium may be manufactured by microencapsulation techniques such as complex coacervation which is capable of producing microcapsules of between 10 and 800 microns in diameter.

Two possible encapsulation techniques are fluidised bed spray coating and spray congealing.

Using fluidised bed spray coating it has been possible to produce encapsulated particles in the correct size range, for example consisting of 75% by weight palmitic or stearic acid and 25% potassium chloride or potassium permanganate (the fluidised solid material was 43±10 µm or 98±10 µm).

Using spray congealing techniques, fluid milled potassium chloride particles of less than 10 µm diameter were suspended in palmitic acid and the dispersion sprayed to produce particles in the range 10 to 100 µm.

If embedded within the ingestible particle, the active ingredient is preferably provided in the form of much smaller "sub-particles", evenly distributed throughout the ingestible particle.

If encapsulated within an outer ingestible coating, the active ingredient preferably comprises a core of between about 40 to 60 microns in diameter. The thickness of the coating is preferably between 5 and 40 microns, more preferably about 10 microns.

Where the active ingredient is toxic to the target organism, the preferred toxin is an inorganic solid such as potassium chloride which induces heart attack in certain invading species such as mussels and clams. The potassium chloride is preferably provided in the form of crystals of appropriate size. An alternative to potassium chloride is potassium permanganate.

Alternative toxins include saponins, more preferably "Lemmatoxin" derived from Endod berries, or a synthesised form of its active ingredients. A combination of two or more different toxins, or a toxin combined with one or more further active ingredients, may be used.

The particles are preferably at least partially resistant to water, such that they may be suspended in water without undue leaching of the active ingredient into the water, for example they should retain at least 75% of the active ingredient when immersed in water for several hours.

The carrier material may conveniently be manufactured from starch, such as potato starch, which may be provided in the form of a paste, or chocolate which is preferably 70% cocoa solids. Alternative ingestible carrier materials suitable for making the particles include beeswax, fatty acids such as palmitic acid, stearic acid, oils, fats and waxes or derivatives thereof, or dried plankton, e.g. dried phytoplankton or dried zooplankton. Clearly, the nature of the ingestible substance will vary dependent upon the target organism, and is preferably a material which is both nutritious and attractive to the particular target organism. Any combination of two or more of the aforesaid substances may be used. A carrier material including or comprising one or more fatty acids is particularly preferred as it forms a hard coating and is slightly soluble in water, thus allowing the particles to remain active for their residence time in the water. For example, a 100 µm stearic acid particle will dissolve in stagnant water in 124 hours.

Preferably the particles have neutral buoyancy in freshwater, corresponding to an optimum density for the particles of 1 g/cm$^3$, which can be achieved using, for example 26% KCl in palmitic acid or 11% KCl in stearic acid. The hydrophobicity of such particles inhibits dispersal in water but dispersal may be facilitated by the is use of a surfactant such as sodium palmitate at around 1 wt % of the particles.

According to a second aspect of the present invention there is provided a method of inducing an invertebrate organism to ingest a substance having desired biological activity in the organism when ingested by the organism, the method including introducing into the organism's environment particles ingestible by the organism and including the substance and at least one carrier material, wherein the substance is solid and coated with or encapsulated within the carrier material and wherein the substance is toxic to the target organism.

The method preferably includes the step of contacting the organisms with the particles for at least 4 hours, more preferably for between 4 and 8 hours.

According to this second aspect of the present invention there is further provided a method of concentrating, to a biologically active concentration within an invertebrate organism, at least one substance, the method comprising providing in the organism's environment particles containing the substance and at least one carrier material, the particles being ingested by the organism such as to effect said concentration of the substance, wherein the substance is solid and coated with or encapsulated within the carrier material and wherein the substance is toxic to the target organism.

According to a third aspect of the present invention there is provided a method of preventing cessation of feeding in an invertebrate organism which would otherwise occur due to the presence of a substance in the organism's environment, the method including the step of providing the substance in the form of particles ingestible by the organism, said particles also including a carrier material, wherein the substance is solid and coated with or encapsulated within the carrier material and wherein the substance is toxic to the target organism.

Thus, because the organism continues to feed, the substance is effectively concentrated within the organism and reduces the total amount of substance required to be added to the organism's environment to have the desired effect on the organism.

According to a fourth aspect of the present invention there is provided a method of controlling an invasive or potentially invasive population of invertebrate organisms, comprising feeding said population with an effective amount of a composition comprising particles containing a carrier material and at least one active ingredient, wherein the active ingredient is solid and coated with or encapsulated within the carrier material and wherein the active ingredient is toxic to the target organism.

By "effective amount" it is meant sufficient to have a desired biological effect on the population or on individuals within the population.

Preferably, said active ingredient is toxic to the target organism and the effective amount is a sufficient amount to kill a significant number of individuals within the population, or to reduce the tendency of the population to is become or remain invasive, for example in the case of mussels, their tendency to adhere to each other (aggregation) and/or to the underlying substrate.

Where individual organisms are killed, death may occur either during the treatment of the present invention or sometime after treatment as a direct or indirect result of the treatment.

According to a fifth aspect of the present invention there is provided a method of treating water containing invertebrate organisms, comprising adding to the water particles containing at least one carrier material and at least one active ingredient, said particles being ingestible in an effective amount by the invertebrate organisms, wherein the active ingredient is solid and coated with or encapsulated within the carrier material and wherein the active ingredient is toxic to the target organism.

Preferably, the particles, or at least the carrier material, are/is at least partially resistant to water such that the active ingredient is inhibited from leaching into the water for sufficient time for an effective amount of the composition to be ingested by the target organisms.

According to a sixth aspect of the present invention there is provided a method of controlling parasites or symbionts in or on a host invertebrate organism, the method comprising feeding the host organism with particles including at least one carrier material and at least one active ingredient having biological activity in the host and/or in the parasite or symbiont, wherein the active ingredient is solid and coated with or encapsulated within the carrier material and wherein the active ingredient is toxic to the target organism.

According to an seventh aspect of the present invention there is provided a method of rendering an environment suitable for the farming of invertebrate organisms, the method comprising adding to the environment particles containing at least one carrier material and at least one active ingredient, said particles being ingestible by the organisms, wherein the active ingredient is solid and coated with or encapsulated within the carrier material and wherein the active ingredient is toxic to the target organism.

Preferably, said active ingredient is a nutrient or growth factor.

According to a eighth aspect of the present invention there is provided a food product for the farming of invertebrate organisms, the food and product comprising particles ingestible by the organisms having at least one active ingredient and at least one carrier material, wherein the active ingredient is solid and coated with or encapsulated within the carrier material and wherein the active ingredient is toxic to the target organism.

Preferably, the particles include several nutrients relevant to the nutritional requirements of the organisms to be farmed.

Any feature of any aspect of any invention or embodiment described herein may be combined with any other feature of any aspect of any invention or embodiment described herein.

Embodiments of the present invention will now be described, by way of example only, with reference to the accompanying drawings, in which.

Figure 6:
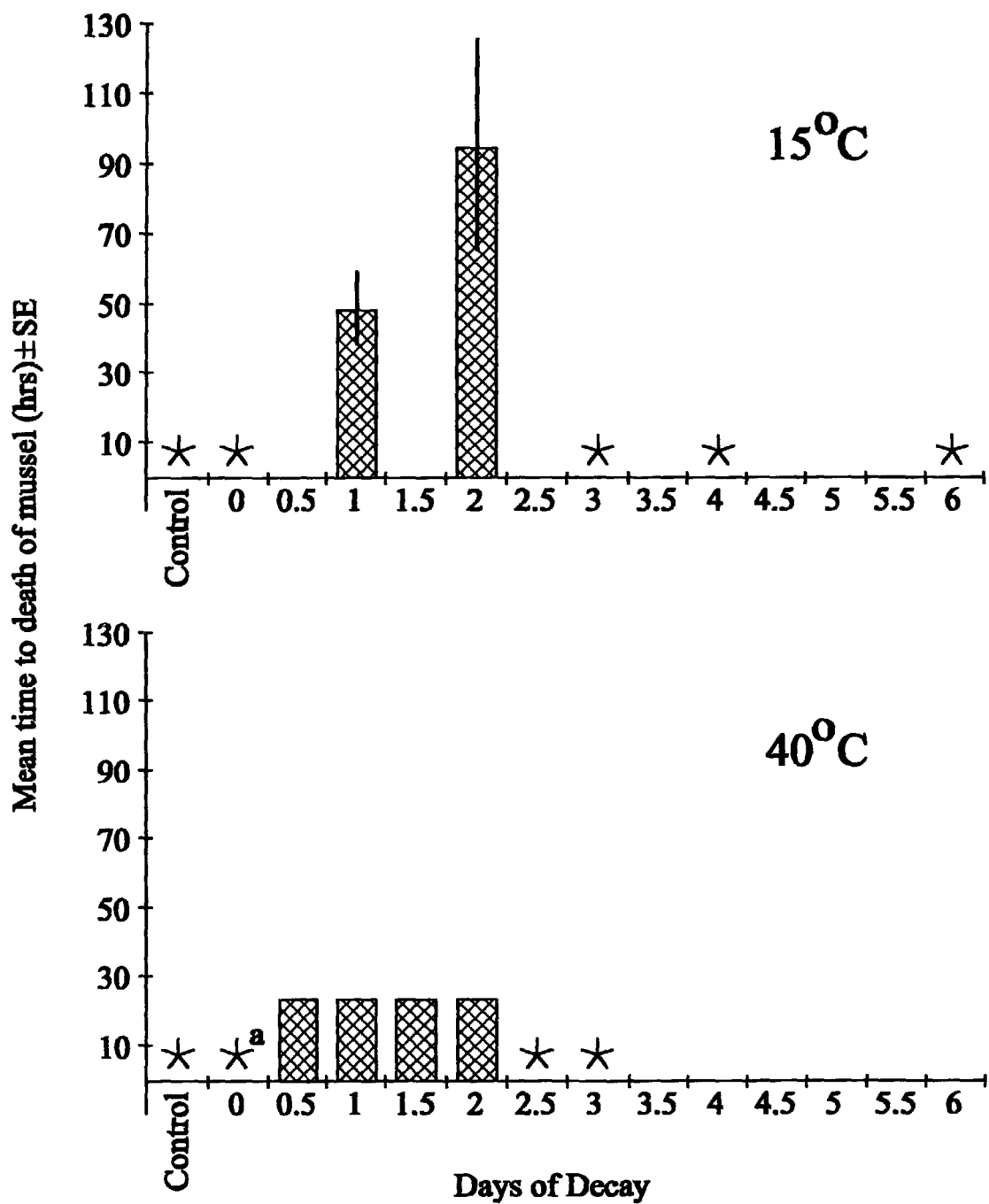

FIG. 6 comprises two graphs of mean time for Zebra mussels to die when exposed to 30 mg/l Endod that had been allowed to decay in water for differing numbers of days. Endod was decayed at 15° C. and 40° C. (Asterisks denote experiments that were run where no Zebra mussels died, $^a$ denotes an experiment where a single Zebra mussel died.

Figure 7:
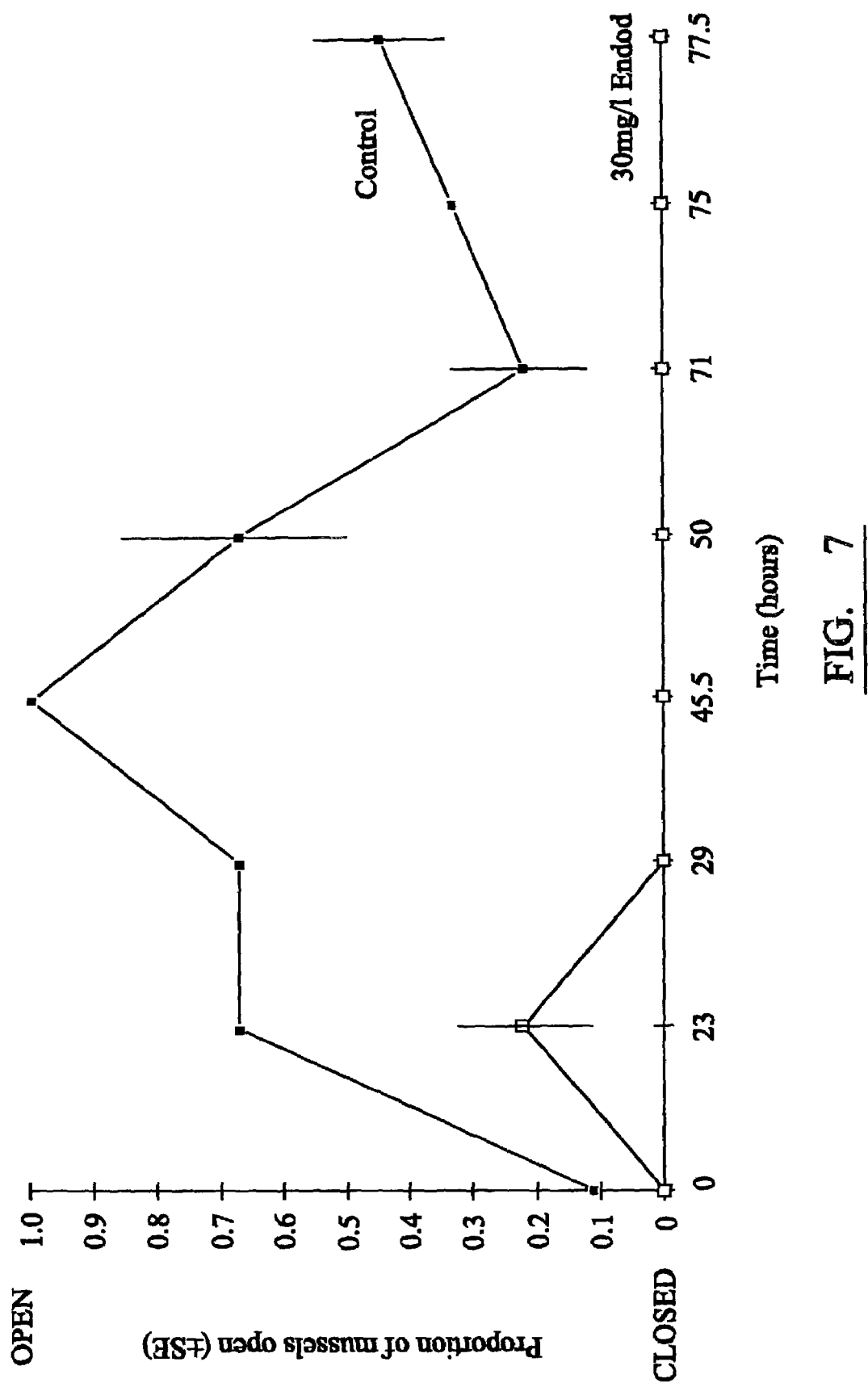

FIG. 7 is a graph of the proportion of Zebra mussels that were observed to be open or closed when placed in filtered pond water or filtered pond water with lethal doses of Endod.

Figure 8:

FIG. 8 is a photograph of a Zebra mussel which has been exposed to water containing a suspension of oil paint in vegetable oil. The arrow indicates the gut, which has become stained with the ingested particles of pigment.

Figure 9:
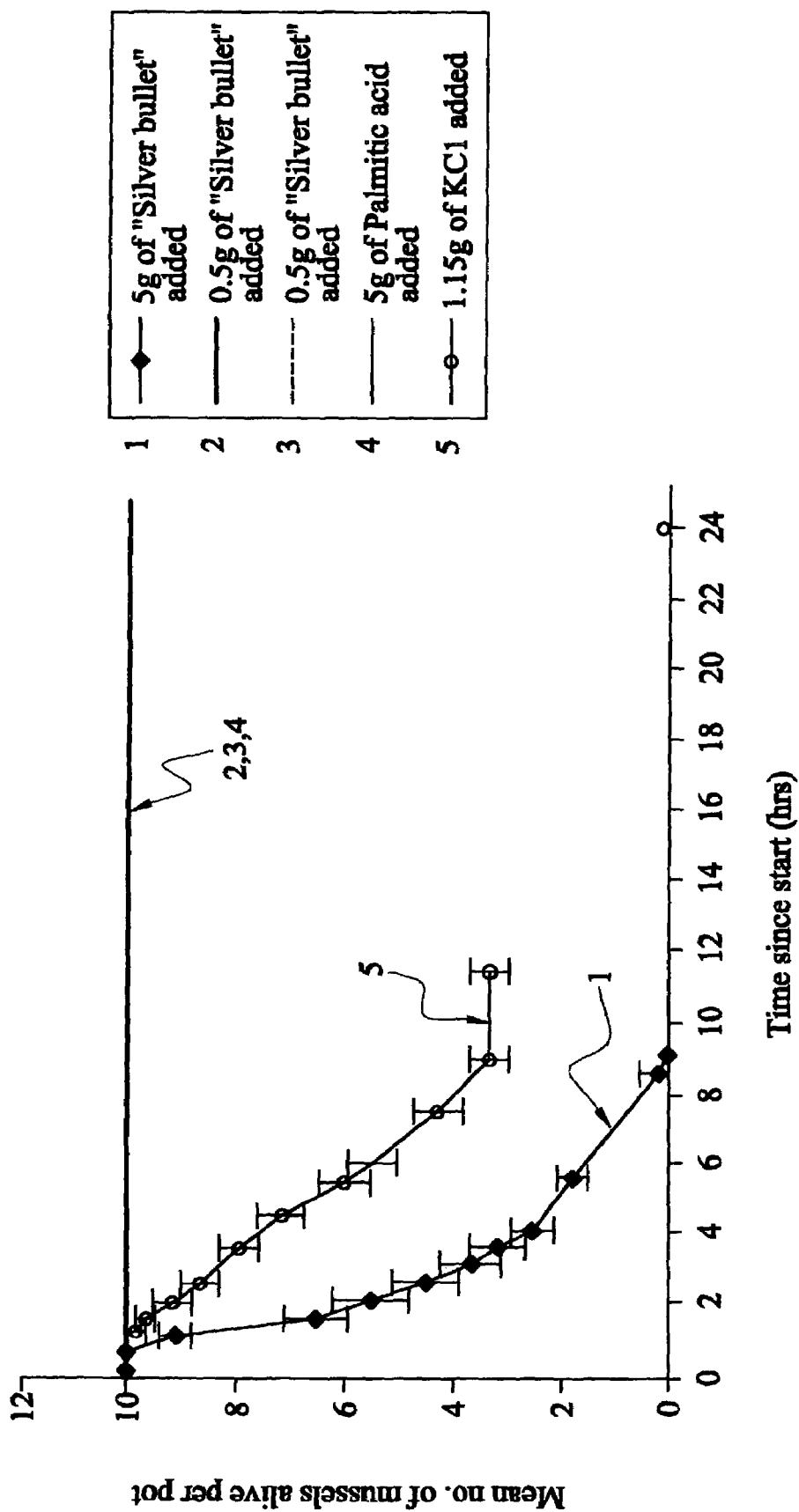

FIG. 9 is a graph of mean numbers of mussels alive during Experiment 8.

Figure 10:
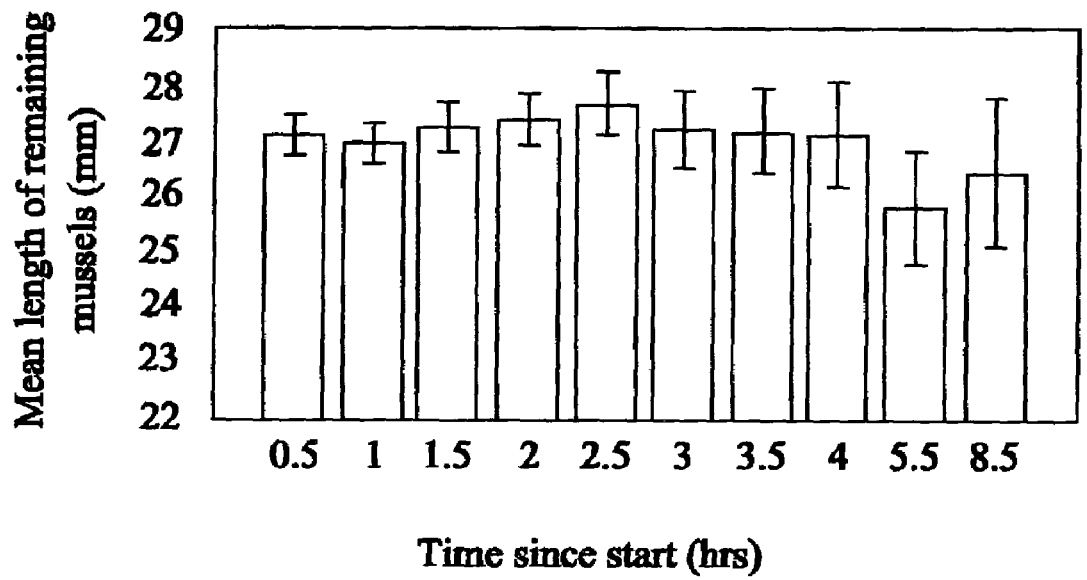

FIG. 10 is a graph of the mean lengths of remaining mussels at intervals during Experiment 8.

Figure 11:
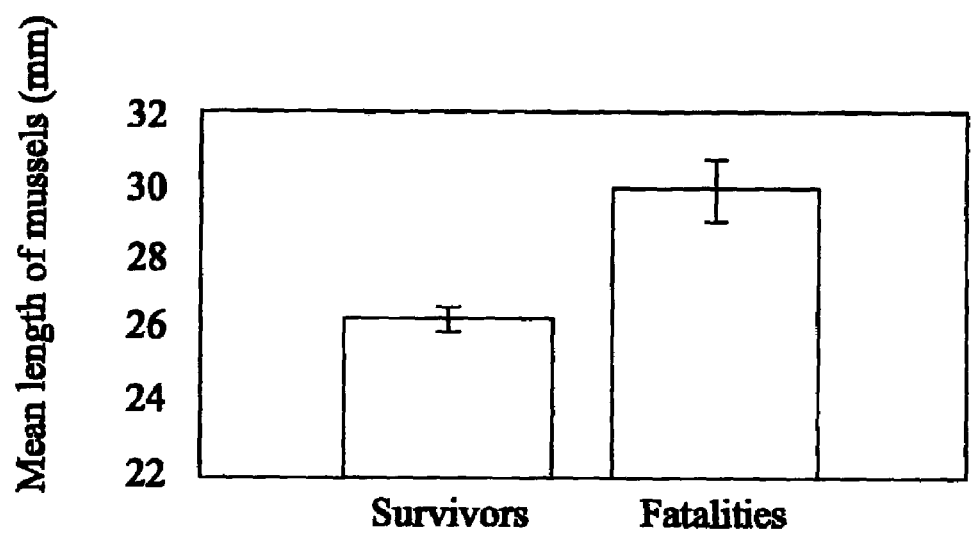

FIG. 11 is a comparison of the mean sizes of survivors of fatalities after Experiment 8.

FIGS. 12 to 16 are scanning electron micrographs (SEMs) of particles in accordance with the present invention.

Figure 17:
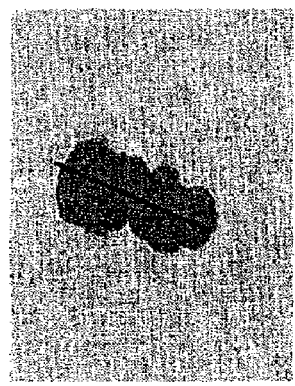
Figure 17:
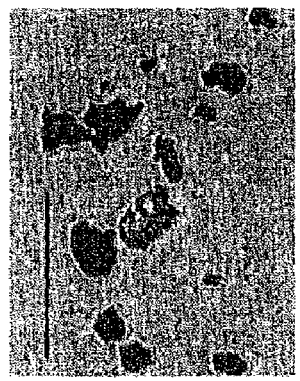
Figure 17:
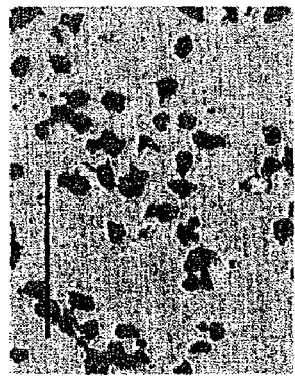
Figure 17:
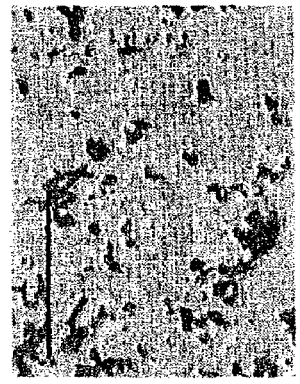
Figure 17:
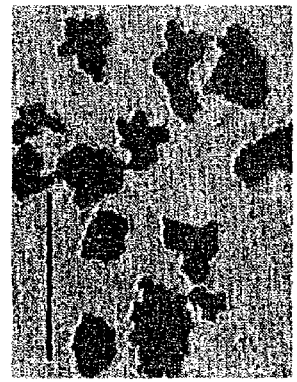
Figure 17:
Figure 17:
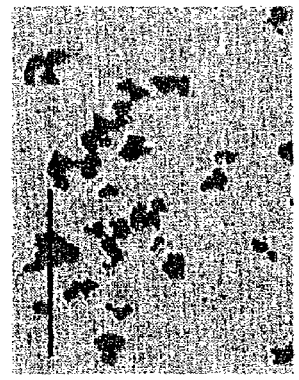
Figure 17:
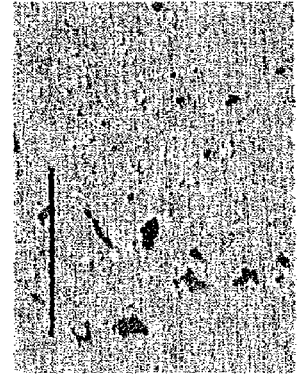

FIG. 17 is a series of photomicrographs of particles from two different samples of particles during size fractionation.

Figure 1:
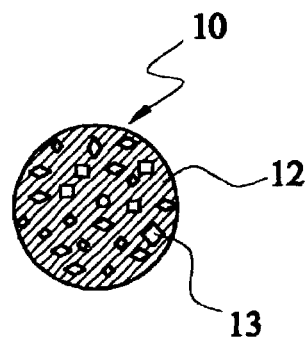
FIG. 1 illustrates a particle having an active ingredient homogeneously embedded therein, in accordance with the present invention.

Each of the particles, or at least a substantial percentage thereof, making up the composition and for use in the method of the present invention may comprise a particle 10 (see FIG. 1) of carrier material 12 such as chocolate (a substance edible by the target organism, for example the Zebra mussel (*Dreissena polymorpha*)), within which is embedded much smaller "sub-particles" 13 of an active ingredient, in the case of the Zebra mussel, potassium chloride KCl crystals. The preferred size of the particle 10 is about 100 microns in diameter.

Other preferred carrier materials include dried phytoplankton or dried zooplankton.

A more preferred type of particle 10' is that shown in FIG. 2 in which a core 14 of a single KCl crystal of about 53 micron diameter, surrounded by a carrier material (e.g. chocolate) coating 16, the whole being then ground back down to approximately 90 micron diameter.

FIG. 2*a* illustrates an alternative method of producing particles according to the present invention, in which starch powder 20 is mixed with distilled water 22 (or Kcl solution, for a toxic particle), extruded through a die 24 to make flake 26 which is then passed with zirconia balls through a pulverizer 28 and passed through a 75 μm sieve 30 to produce particles of diameter ≦75 μm.

Experiment 1

The toxicity of KCl alone to Zebra mussels is illustrated in Table 1 below, which gives the results of the following experiment:

1) A series of pots where filled with 20 ml of distilled water plus a specified mass of KCl crystals, ground to less than 53 microns. The masses of KCl were chosen to represent the total amount of KCl that would be ingested by a mussel filtering 1 litre of water per day.

2) One mussel was placed in each pot (it was assumed that the mussel would continuously re-filter the limited amount of solution in the pot and thus ingest the required amount of KCl.

3) The mussels were observed at intervals during the following two days, and their state noted (alive, dead or closed, i.e mussel still alive but temporarily ceased feeding).

TABLE 1

Toxicity of different masses of KCl to Zebra mussels over two days.

| | Date | | | |
|---|---|---|---|---|
| | 17/03/99 | 18/03/99 | 18/03/99 | 19/03/99 |
| Mass of KCl | Time | | | |
| (mg) | 16:30 | 11:30 | 13:30 | 16:00 |
| 0 (control) | Alive | Closed | Alive | Dead |
| 50 | Alive | Dead | Dead | Dead |
| 25 | Alive | Dead | Dead | Dead |

TABLE 1-continued Toxicity of different masses of KCl to Zebra mussels over two days.

| Mass of KCl (mg) | Date | | | |
|---|---|---|---|---|
| | 17/03/99 | 18/03/99 | 18/03/99 | 19/03/99 |
| | Time | | | |
| | 16:30 | 11:30 | 13:30 | 16:00 |
| 10 | Alive | Alive | Closed | Dead |
| 5 | Alive | Alive | Alive | Alive |
| 1 | Alive | Alive | Alive | Alive |
| 0.5 | Alive | Alive | Closed | Alive |
| 0.1 | Alive | Alive | Alive | Alive |

As can be seen from the above table, using KCl alone is not effective over the test period at lower concentrations. The aim of the invention is to reduce the concentrations down to less than 1% of bulk concentration, which corresponds to the 0.5 mg mass in Table 1, which clearly would not have the desired effect of controlling the mussels using KCl alone.

Experiment 2

The toxicity of an alternative toxin was also investigated and compared with that of KCl. In an another experiment, the results of which are shown in Table 2 and illustrated in the graph of FIG. 3, Endod was ground to approximately 75 micron particle size which was then fed to a sample group of five mussels and was shown to achieve total mortality of the mussels at low Endod concentrations over a period of approximately 5 days.

TABLE 2 toxicity of Endod to Zebra mussels compared with KCl

| Toxin | Mass of toxin (mg) | Time for mortality of all mussels (hours) |
|---|---|---|
| Endod | 0 | — |
| Endod | 0.5 | 102 |
| Endod | 7.5 | 30.5 |
| Endod | 25 | 23 |
| Endod | 100 | 102 (80% mortality) |
| Potassium Chloride | 100 | 8 (60% mortality) |

One particular advantage of Endod as a toxin is its ability to achieve latent mortality (death after Endod has left the system) in Zebra mussels. Powder from dried Endod berries is lethal to Zebra mussels and those that did not die failed to reaggregate and reattach (Lemma et al, 1991). A short dose for 4-8 hours provides 50% mortality plus continuing resultant mortality. Endod can also be easily adsorbed using activated charcoal beds, but does not as yet have regulatory approval for its use in cooling water systems. Toxicity of Endod to other, non target organisms compared with Zebra mussels is shown in Table 3, which gives both the 48 hour $LC_{50}$ value as well as the 95% confidence interval (the 48 h-$LC_{50}$ is the concentration of toxin required to induce mortality in 50% of the population within 48 hours).

TABLE 3

Toxicity of Endod to target and non target organisms (taken from Waller, Rach, Cope and Marking 1993: Toxicity of Candidate Molluscicides to Zebra Mussel and Selected Non-target organisms).

48-hour $LC_{50}$ and 95% confidence interval

| | Zebra Mussel | Rainbow | Channel | Threehorn |
|---|---|---|---|---|
| | 20-25 mm | Trout 5-8 mm | Catfish 0.8-1.2 g | Wartyback 30-50 mm |
| KCl | 150 | 147 | 1610 | 720 | >2000[a] |
| | 129-175 | 132-163 | 1223-2119 | 588-882 | |
| Endod | >10[a] | 9.51 | 1.31 | 1.60 | >30[a] |
| | | 8.50-10.65 | 1.12-1.53 | 1.23-2.08 | |

[a]Less than 50% mortality in the highest test concentration.

Experiment 3

Lethal concentrations of Endod were identified in the following experiment.

Six pots, each containing three Zebra mussels of approximately 2 cm length, were filled with 100 ml of filtered pond water. Each pot was continually aerated and held at a constant 15° C. Mussels were allowed to acclimatise for two hours before different masses of ≦75 μm Endod powder (from dried berries) was added to five of the pots (0.002 g, 0.005 g, 0.01 g, 0.03 g, 0.1 g). The sixth pot served as a control. The number of mussels that were dead in each pot was monitored regularly over 4.5 days. The observations are shown below in Table 4 and these results are presented graphically in FIGS. 4 and 5.

Results

TABLE 4

Establishing ball park lethal dose of Endod required.

| | | O = Open | | C = Closed | | | D = Dead | |
|---|---|---|---|---|---|---|---|---|
| Day | Time | 2 mg Endod/liter | 5 mg | 10 mg | 30 mg | 100 mg | Control | Time (hrs) |
| Wed | 3:00 pm | 1O 2C | 3C | 3O | 3C | 3C | 3C | 0.5 |
| | 3:30 pm | 2O 1C | 3C | 3C | 3C | 3C | 3O | 1 |
| | 4:00 pm | 2O 1C | 2O 1C | 3C | 3C | 3C | 3O | 1.5 |
| | 4:30 pm | 2O 1C | 3O | 1O 2C | 3C | 3C | 3O | 2 |
| | 5:30 pm | 3O | 2O 1C | 1O 2C | 3C | 3C | 3O | 3 |
| | 6:00 pm | 3O | 3C | 3C | 3C | 3C | 3O | 3.5 |
| | 6:30 pm | 3O | 2O 1C | 3C | 3C | 3C | 3O | 4 |
| | 7:30 pm | 2O 1C | 1O 2C | 3C | 3C | 3C | 2O 1C | 5 |
| | 10:30 pm | 2O 1C | 1O 2C | 1O 2C | 1O 2C | 3C | 2O 1C | 8 |

TABLE 4-continued

Establishing ball park lethal dose of Endod required.

| | | O = Open | | C = Closed | | | D = Dead | |
|---|---|---|---|---|---|---|---|---|
| Day | Time | 2 mg Endod/liter | 5 mg | 10 mg | 30 mg | 100 mg | Control | Time (hrs) |
| Thur | 9:00 am | 2O 1C | 1O 2C | 3C | 3D | 3D | 2O 1C | 18.5 |
| | 12noon | 1O 2C | 1D 2C | 3C | 3D | 3D | 2O 1C | 21 |
| | 2:30 pm | 1O 2C | 1D 1O1C | 3C | | | 1O 2C | 23.5 |
| | 3:00 pm | 1O 2C | 1D 2C | 1D 2C | | | 1O 2C | 24 |
| | 3:30 pm | 3C | 2D 1C | 1D 2C | | | 1O 2C | 24.5 |
| | 4:00 pm | 1O 2C | 2D 1C | 1D 2C | | | 2O 1C | 25 |
| | 4:30 pm | 3C | 2D 1C | 2D 1C | | | 2O 1C | 25.5 |
| | 5:30 pm | 1O 2C | 2D 1O | 2D 1C | | | 2O 1C | 26.5 |
| | 9:00 pm | 3C | 2D 1C | 2D 1C | | | 1O 2C | 30 |
| | 10:00 pm | 1O 2C | 2D 1C | 2D 1C | | | 2O 1C | 31 |
| Fri | 9:00 am | 3C | 2D 1C | 2D 1C | | | 3O | 42 |
| | 10:30 am | 1O 2C | 2D 1C | 2D 1C | | | 3O | 43.5 |
| | 11:30 am | 3O | 2D 1C | 2D 1C | | | 2O 1C | 44.5 |
| | 3:00 pm | 3O | 2D 1C | 3D | | | 1O 2C | 48 |
| Sat | 10:00 am | 3D | 3D | 3D | | | 2O 1C | 67 |
| Sun | 9:00 am | 1O 2C | 3D | | | | 3O | 102 |
| Mon | 10:00 am | 2O 1C | 3D | | | | 2O 1C | 115 |
| Tues | 10:00 am | 3O | 3D | 3D | 3D | 3D | 3C | 139 |
| | 10:00 pm | 3O | | | | | 2O 1C | 151 |
| Wed | 9:00 am | 3O | | | | | 1O 2C | 162 |
| | 11:00 pm | 1O 2C | | | | | 1O 2C | 176 |
| Thur | 11:30 am | 3C | | | | | 3C | 188.5 |
| | 4:00 pm | 2O 1C | | | | | 2O 1C | 193 |
| Fri | 9:00 am | 2O 1C | | | | | 3O | 212 |
| Sat | 4:00 pm | 2O 1C | | | | | 3O | 231 |
| | 10:30 pm | 3C | | | | | 1O 2C | 237.5 |
| Sun | 9:00 pm | 2O 1C | | | | | 1O 2C | 260 |
| Mon | 9:00 am | 2O 1C | | | | | 1O 2C | 272 |

Figure 4:
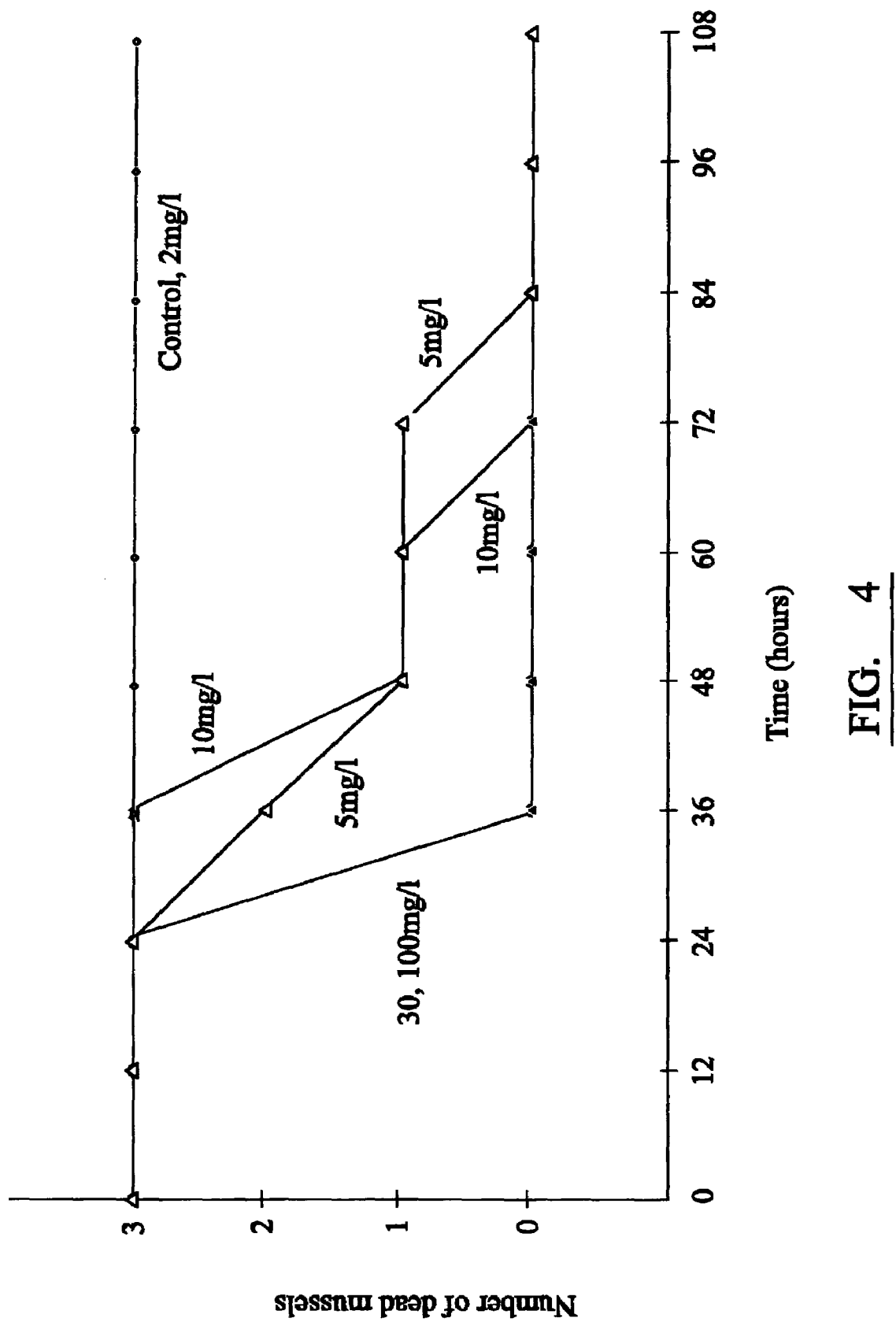
FIG. 4 is a graph of time taken for three Zebra mussels to die when exposed to different concentrations of Endod.
Figure 5:
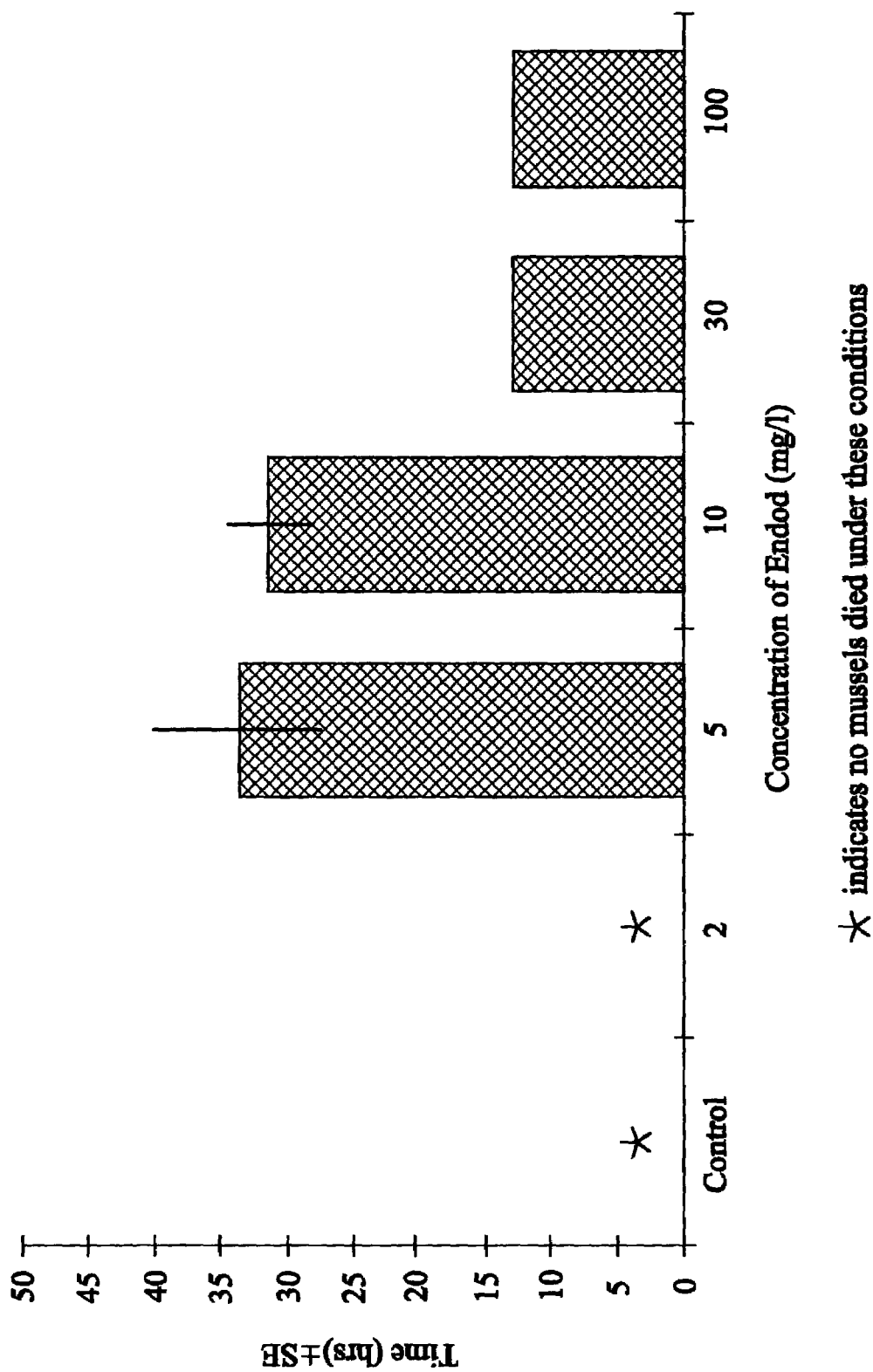
FIG. 5 is a graph of mean time for Zebra mussels to die with different concentrations of Endod.

No mussels died in the control pot, or with Endod at 2 mg/l (FIGS. 4 and 5). All mussels had died within 36 hours where the mussels experienced 30 and 100 mg/l Endod and all mussels had died by 84 hours at 5 mg/l Endod (FIG. 4). Mussels died most quickly at the highest concentrations of Endod (FIG. 5).

Experiment 4

In this experiment it was assessed how quickly Endod biodegrades under different temperature regimes. Once it had been established from experiment 3 that 30 mg/litre Endod was lethal to Zebra mussels, six sets of three pots were filled with 100 ml filtered pond water and 0.03 g ≦75 μm Endod powder and held at a constant 15° C. The Endod was allowed to decay in the pots for 6, 4, 3, 2, 1 and 0 days after which the water was poured through filter paper and the residue resuspended in 100 ml filtered pond water. This ensured that toxins associated with the bacterial breakdown of the Endod did not interfere with the experiment. Three Zebra mussels (approximately 2 cm length) were added to each pot, the pots held at a constant 15° C., and the mussels observed at regular intervals. At each inspection, the number of mussels that were dead was recorded. Observations were made over six hours or until all mussels had died.

The experiment was repeated with Endod which was allowed to decay at a constant 40° C. over 3, 2.5, 2, 1.5, 1. 0.5 and 0 days. Once mussels were added to the pots they were transferred to a constant 15° C. Observations were made over 33 hours. The observations are shown in tables 5 and 6 and these results are shown graphically in FIG. 6.

Results

AppenDix 1—Decay at 15 C.

TABLE 5

| | | Time(Days) | | | | | |
|---|---|---|---|---|---|---|---|
| Time(hrs) | CONTROL | 6 | 4 | 3 | 2 | 1 | 0 |
| 0 | 3C | 3C | 3C | 3C | 3C | 3C | 2C 1O |
| | 3C | 3C | 3C | 2C 1O | 3C | 3C | 3C |
| | 2C 1O | 3C | 3C | 2C 1O | 2C 1O | 3C | 3C |
| 23 | 2O 1C | 2O 1C | 3O | 2O 1C | 1D 2C | 1D 2C | 3C |
| | 2O 1C | 3O | 1O 2C | 2O 1C | 1O 2C | 1O 2C | 1O 2C |
| | 2O 1C | 1O 2C | 2O 1C | 2O 1C | 1O 2C | 1O 2C | 2O 1C |
| 29 | 2O 1C | 3O | 2O 1C | 3O | 1D 2C | 1D 2C | 2O 1C |
| | 2O 1C | 3O | 3O | 1O 2C | 3C | 1D 2C | 1O 2C |
| | 2O 1C | 2O 1C | 2O 1C | 2O 1C | 3C | 1O 2C | 3C |

TABLE 5-continued

|  | Time(Days) | | | | | | |
|---|---|---|---|---|---|---|---|
| Time(hrs) | CONTROL | 6 | 4 | 3 | 2 | 1 | 0 |
| 45.5 | 3O | 2O 1C | 2O 1C | 1O 2C | 2D 1C | 2D 1C | 3C |
|  | 3O | 3O | 2C 1O | 1O 2C | 3C | 3D | 3C |
|  | 3O | 2O 1C | 3O | 3O | 3C | 1D 2C | 1O 2C |
| 50 | 2O 1C | 1O 2C | 3O | 3O | 2D 1C | 2D 1C | 2O 1C |
|  | 3O | 1O 2C | 3O | 2O 1C | 3C | 3D | 1O 2C |
|  | 1O 2C | 2O 1C | 2O 1C | 3O | 3C | 2D 1C | 2O 1C |
| 71 | 1O 2C | 2O 1C | 1O 2C | 1O 2C | 3D | 2D 1C | 3O |
|  | 3C | 3C | 3O | 1O 2C | 3C | 3D | 2O 1C |
|  | 1O 2C | 3C | 2O 1C | 2O 1C | 3C | 2D 1C | 2O 1C |
| 75 | 1O 2C | 1O 2C | 3O | 2O 1C | 3D | 3D | 3O |
|  | 1O 2C | 3C | 2O 1C | 2O 1C | 3C | 3D | 3O |
|  | 1O 2C | 3C | 2O 1C | 3C | 3C | 2D 1C | 3O |
| 77.5 | 2O 1C | 1O 2C | 1O 2C | 1O 2C | 3D | 3D | 2O 1C |
|  | 1O 2C | 3C | 3O | 2O 1C | 3C | 3OD | 1O 2C |
|  | 1O 2C | 3C | 2O 1C | 1O 2C | 3C | 2D 1C | 1O 2C |
| 78.5 | 3O | 2O 1C | 3O | 3C | 3D | 3D | 2O 1C |
|  | 2O 1C | 3C | 2O 1C | 1O 2C | 1O 2C | 3D | 2O 1C |
|  | 2O 1C | 2O 1C | 2O 1C | 3C | 1O 2C | 2D 1O | 2O 1C |
| 91 | 2O 1C | 1O 2C | 3O | XXX | 3D | 3D | 3O |
|  | 1O 2C | 2O 1C | 2O 1C | 1O 2C | 1O 2C | 3D | 3O |
|  | 1O 2C | 1O 2C | 2O 1C | 3C | 2O 1C | 2D 1C | 3O |
| 93 | 2O 1C | 3C | 3O | XXX | 3D | 3D | 3O |
|  | 1O 2C | 1O 2C | 1O 2C | 1O 2C | 1O 2C | 3D | 2O 1C |
|  | 1O 2C | 1O 2C | 2O 1C | 3C | 3C | 2D 1C | 3O |
| 94 | 1O 2C | 3C | 3O | XXX | 3D | 3D | 1O 2C |
|  | 1O 2C | 3O | 2O 1C | 3C | 3C | 3D | 2O 1C |
|  | 1O 2C | 2O 1C | 2O 1C | 3C | 3C | 2D 1C | 2O 1C |
| 116 | 3C | 1O 2C | 1O 2C | XXX | 3D | 3D | 3C |
|  | 3C | 1O 2C | 1O 2C | 3C | 3C | 3D | 3C |
|  | 2O 1C | 3C | 1O 2C | 3C | 1D 2C | 2D 1C | 2O 1C |
| 122 | 3C | 3C | 2O 1C | XXX | 3D | 3D | 1O 2C |
|  | 3C | 1O 2C | 2O 1C | 1O 2C | 3C | 3D | 1O 2C |
|  | 1O 2C | 1O 2C | 1O 2C | 3C | 3D | 3D | 3C |
| 126 | 3C | 2O 1C | 3O | XXX | 3D | 3D | 3C |
|  | 2O 1C | 1O 2C | 3O | 1O 2C | 3C | 3D | 3C |
|  | 2O 1C | 3C | 2O 1C | 1O 2C | 3D | 3D | 1O 2C |
| 138 | 3O | 1O 2C | 1O 2C | XXX | 3D | 3D | 3C |
|  | 3C | 3C | 1O 2C | 1O 2C | 2D 1C | 3D | 1O 2C |
|  | 3C | 1O 2C | 3C | 1O 2C | 3D | 3D | 1O 2C |
| 146 | 2O 1C | 3C | 2O 1C | XXX | 3D | 3D | 1O 2C |
|  | 2O 1C | 3C | 3C | 1O 2C | 3D | 3D | 2O 1C |
|  | 1O 2C | 1O 2C | 1O 2C | 1O 2C | 3D | 3D | 1O 2C |

AppenDix 1—Decay at 40 C.

TABLE 6

|  | Time (Days) | | | | | | |
|---|---|---|---|---|---|---|---|
| Time(hrs) | 3 | 2.5 | 2 | 1.5 | 1 | 0.5 | 0 |
| 0 | 3C | 3C | 3C | 3C | 3C | 1O 2C | 3C |
|  | 3C | 3C | 3C | 3C | 3C | 3C | 3C |
|  | 3C | 3C | 3C | 3C | 1O 2C | 3C | 3C |
| 13.5 | 3C | 3C | 3C | 1O 2C | 1O 2C | 3C | 3O |
|  | 3C | 2O 1C | 3C | 3C | 3C | 1O 2C | 3C |
|  | 3C | 1O 2C | 3C | 3C | 3C | 3C | 3C |
| 32 | 2O 1C | 1O 2C | 3D | 3D | 3D | 3D | 1D 2C |
|  | 2O 1C | 1O 2C | 3D | 3D | 3D | 3D | 3C |
|  | 1O 2C | 3C | 3D | 3D | 3D | 3D | 3C |

Endod remained active up until two days, after which the Endod did not kill any mussels. This result held true under both temperature regimes (FIG. 6). At 15° C. mussels died more quickly with Endod that had been held in water for only one day compared with two days. Mussels placed with Endod which had been allowed to decay for 0 days (i.e. the Endod was suspended in water and then immediately filtered) resulted in only one mortality from the six pots (eighteen mussels). No mussels died in control pots.

Experiment 5

In this experiment Zebra mussels were tested to see if they showed this closing response in the presence of Endod.

At each inspection during experiment 4, it was recorded how many mussels were closed or were open and respiring normally.

Results

After 77.5 hours, all but one of the nine mussels exposed to Endod had died. Mussels exposed to Endod remained closed for almost the entire experimental period, while a large proportion of the mussels in control pots were open for the majority of time (FIG. 7).

Experiment 6

In this experiment it was tested whether novel, marked organic particles were ingested by live Zebra mussels.

A suspension of marked organic particles was produced by mixing vegetable oil with red pigmented oil paint and stirring this into filtered pond water. Approximately twenty Zebra mussels (lengths approximately 0.5-3 cm) were added to the suspension and left for 48 hours, after which the mussels were killed and opened.

Results

A large proportion of the Zebra mussels were seen to be open at all times during the course of the experiment. On opening the mussels it was clear that many had ingested the marked particles by the presence of a red gut showing through the wall of the visceral mass (FIG. 8). It was less clear to observe by eye the red guts of the smallest mussels, although dissection of the visceral mass often revealed the presence of red particles within the gut lumen.

The results of experiments 3 to 6 provide strong support for the feasibility of an encapsulated product. It has been shown that Zebra mussels close-up in the presence of raw, non-capsulated toxins such as Endod and therefore an encapsulated product should reduce greatly the amount of toxin that would be required to induce mortality compared with simply dumping toxins into the water. It has also been shown that novel organic particles can be taken into the guts of Zebra mussels of all sizes.

Endod proved to be an effective toxin, inducing mortality at concentrations >2 mg/l. In theory, this lethal concentration of Endod can be reduced significantly if the toxin is encapsulated as proposed. It is promising that Endod biodegrades after two days in the water column, irrespective of water temperature. This means that Endod will not bioaccumulate in the ecosystem and therefore makes it a highly suitable product to use in closed systems such as the Great Lakes. It is also promising that Endod remains active at temperatures as high as 40° C., because this means that it will remain active within the heated waters of power stations.

Experiment 7

Figure 2:
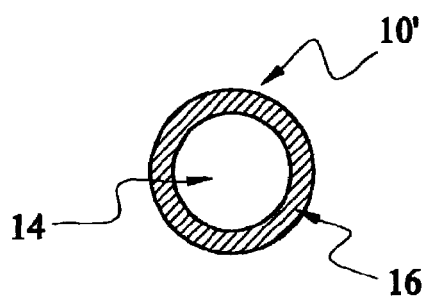
FIG. 2 illustrates a particle having a core of active ingredient surrounded by an edible coating.

Two types of particles containing KCl and chocolate mixtures were prepared. One type of particle comprised an edible chocolate substrate of about 100 micron diameter, within which was embedded a number of much smaller crystals of KCl (FIG. 1) whereas the other type of particle comprised a single KCl crystal of about 53 micron diameter coated with chocolate and then ground back to about 90 micron diameter (FIG. 2). When these particles were suspended in water in which mussels were kept, three out of four mussels died within two days.

Experiment 8

A batch of particles ("Batch 7") was manufactured by a fluidised bed coating method. 98 μm KCl particles were passed through a 350 μm sieve with 1% silica to help fluidisation. 800 g of solids were sprayed with palmitic acid (MP 61° C.) for 20 minutes at approximately 12 ml min$^{-1}$. 400 g of the resulting solids were then further coated with palmitic acid to finally produce particles containing between 20 and 25% wt of KCl.

40 1-litre beakers were filled with 500 ml of tap water and aerated overnight in a temperature controlled room at 25° C. Ten large Zebra mussels were placed into each beaker, attempting to keep a similar size range in all. Five different treatments were applied (such that each had eight replicates);
1. 5 g of (Batch 7) was added.
2. 0.5 g of (Batch 7) was added.
3. 0.05 g of (Batch 7) was added.
4. 5 g of Palmitic acid alone was added.
5. 1.15 g of KCl (the same amount by mass as in 5 g of Batch 7) was added.

Each treatment substance was thoroughly stirred into each beaker and aeration continued for the duration of the experiment. At reasonably regular intervals, the number of dead mussels (as indicated by gape) were counted in each pot, before being removed and measured. This was continued until most were dead, or 72 hours had elapsed.

The results are shown in Tables 7, 8 and 9 below and represented graphically in FIGS. 9, 10 and 11. Lines 1 to 5 correspond to treatments 1 through 5 respectively.

TABLE 7

| | Length of mussels dying over time when exposed to 5 g of Batch 7 | | | | | | | | | |
|---|---|---|---|---|---|---|---|---|---|---|
| Time(Hrs) | C1 0 | C2 0.5 | C3 1 | C4 1.5 | C5 2 | C6 2.5 | C7 3 | C8 3.5 | C9 4 | C10 8.5 |
| 1 | 32 | 25 | 23 | 25 | 28 | 24 | 28 | 27 | 19 | 20 |
| 2 | 27 | 27 | 23 | 25 | 32 | 27 | 30 | 34 | 23 | 24 |
| 3 | 30 | 28 | 28 | 29 | 33 | 28 | 30 | 32 | 26 | 28 |
| 4 | 31 | 26 | 29 | 29 | 28 | 30 | 23 | 32 | 27 | 27 |
| 5 | 27 | 29 | 25 | 25 | 29 | 28 | 26 | 27 | 28 | 32 |
| 6 | 28 | 34 | 27 | 28 | 32 | 30 | 27 | 28 | 20 | 30 |
| 7 | 28 | 22 | 33 | 24 | 25 | 30 | 34 | 19 | 24 | 23 |
| 8 | 25 | 24 | 23 | 24 | 24 | 23 | 32 | 23 | 28 | 29 |
| 9 | 27 | 24 | 25 | 28 | 27 | 26 | 32 | 26 | 27 | 23 |
| 10 | 28 | 25 | 25 | 32 | 28 | 27 | 27 | 27 | 32 | |
| 11 | 26 | 26 | 29 | 33 | 30 | 34 | 28 | 28 | 30 | |
| 12 | 29 | 28 | 29 | 28 | 28 | 32 | 19 | 20 | 23 | |
| 13 | 34 | 27 | 25 | 29 | 30 | 32 | 23 | 24 | 29 | |
| 14 | 22 | 22 | 28 | 32 | 30 | 27 | 26 | 28 | 23 | |
| 15 | 24 | 25 | 24 | 25 | 23 | 28 | 27 | 27 | | |
| 16 | 24 | 30 | 24 | 24 | 26 | 19 | 28 | 32 | | |
| 17 | 25 | 22 | 28 | 27 | 27 | 23 | 20 | 30 | | |
| 18 | 26 | 29 | 32 | 28 | 34 | 26 | 24 | 23 | | |
| 19 | 28 | 25 | 33 | 30 | 32 | 27 | 28 | 29 | | |
| 20 | 27 | 32 | 28 | 28 | 32 | 28 | 27 | 23 | | |
| 21 | 22 | 24 | 29 | 30 | 27 | 20 | 32 | | | |
| 22 | 25 | 23 | 32 | 30 | 28 | 24 | 30 | | | |
| 23 | 30 | 23 | 25 | 23 | 19 | 28 | 23 | | | |
| 24 | 22 | 28 | 24 | 26 | 23 | 27 | 29 | | | |
| 25 | 29 | 29 | 27 | 27 | 26 | 32 | 23 | | | |
| 26 | 25 | 25 | 28 | 34 | 27 | 30 | | | | |
| 27 | 32 | 27 | 30 | 32 | 28 | 23 | | | | |
| 28 | 24 | 33 | 28 | 32 | 20 | 29 | | | | |
| 29 | 23 | 23 | 30 | 27 | 24 | 23 | | | | |
| 30 | 23 | 25 | 30 | 28 | 28 | | | | | |
| 31 | 28 | 25 | 23 | 19 | 27 | | | | | |
| 32 | 29 | 29 | 26 | 23 | 32 | | | | | |
| 33 | 25 | 29 | 27 | 26 | 30 | | | | | |
| 34 | 27 | 25 | 34 | 27 | 23 | | | | | |
| 35 | 33 | 28 | 32 | 28 | 29 | | | | | |
| 36 | 23 | 24 | 32 | 20 | 23 | | | | | |
| 37 | 25 | 24 | 27 | 24 | | | | | | |
| 38 | 25 | 28 | 28 | 28 | | | | | | |
| 39 | 29 | 32 | 19 | 27 | | | | | | |
| 40 | 29 | 33 | 23 | 32 | | | | | | |
| 41 | 25 | 28 | 26 | 30 | | | | | | |
| 42 | 28 | 29 | 27 | 23 | | | | | | |
| 43 | 24 | 32 | 28 | 29 | | | | | | |
| 44 | 24 | 25 | 20 | 23 | | | | | | |
| 45 | 28 | 24 | 24 | | | | | | | |
| 46 | 32 | 27 | 28 | | | | | | | |
| 47 | 33 | 28 | 27 | | | | | | | |
| 48 | 28 | 30 | 32 | | | | | | | |
| 49 | 29 | 28 | 30 | | | | | | | |
| 50 | 32 | 30 | 23 | | | | | | | |
| 51 | 25 | 30 | 29 | | | | | | | |
| 52 | 24 | 23 | 23 | | | | | | | |
| 53 | 27 | 26 | | | | | | | | |
| 54 | 28 | 27 | | | | | | | | |
| 55 | 30 | 34 | | | | | | | | |
| 56 | 28 | 32 | | | | | | | | |
| 57 | 30 | 32 | | | | | | | | |
| 58 | 30 | 27 | | | | | | | | |

TABLE 7-continued

Length of mussels dying over time when exposed to 5 g of Batch 7

| Time(Hrs) | C1 0 | C2 0.5 | C3 1 | C4 1.5 | C5 2 | C6 2.5 | C7 3 | C8 3.5 | C9 4 | C10 8.5 |
|---|---|---|---|---|---|---|---|---|---|---|
| 59 | 23 | 28 | | | | | | | | |
| 60 | 26 | 19 | | | | | | | | |
| 61 | 27 | 23 | | | | | | | | |
| 62 | 34 | 26 | | | | | | | | |
| 63 | 32 | 27 | | | | | | | | |
| 64 | 32 | 28 | | | | | | | | |
| 65 | 27 | 20 | | | | | | | | |
| 66 | 28 | 24 | | | | | | | | |
| 67 | 19 | 28 | | | | | | | | |
| 68 | 23 | 27 | | | | | | | | |
| 69 | 26 | 32 | | | | | | | | |
| 70 | 27 | 30 | | | | | | | | |
| 71 | 28 | 23 | | | | | | | | |
| 72 | 20 | 29 | | | | | | | | |
| 73 | 24 | 23 | | | | | | | | |
| 74 | 28 | | | | | | | | | |
| 75 | 27 | | | | | | | | | |
| 76 | 32 | | | | | | | | | |
| 77 | 30 | | | | | | | | | |
| 78 | 23 | | | | | | | | | |
| 79 | 29 | | | | | | | | | |
| 80 | 23 | | | | | | | | | |

TABLE 8

No. of live mussels in each pot over time when exposed to 5 g of Batch 7 (1.15 g KCl)

| Time (hours) | C1 | C2 0.5 | C3 1 | C4 1.5 | C5 2 | C6 2.5 | C7 3 | C8 3.5 | C9 4 | C10 5.5 | C11 8.5 |
|---|---|---|---|---|---|---|---|---|---|---|---|
| 1 | 10 | 10 | 7 | 6 | 5 | 4 | 4 | 3 | 1 | 0 | 0 |
| 2 | 10 | 9 | 4 | 3 | 3 | 2 | 1 | 1 | 1 | 0 | 0 |
| 3 | 10 | 8 | 6 | 4 | 2 | 1 | 1 | 1 | 1 | 1 | 0 |
| 4 | 10 | 9 | 8 | 7 | 6 | 5 | 4 | 4 | 3 | 2 | 0 |
| 5 | 10 | 9 | 5 | 4 | 3 | 3 | 2 | 2 | 1 | 0 | 0 |
| 6 | 10 | 10 | 9 | 8 | 6 | 4 | 4 | 3 | 2 | 1 | 0 |
| 7 | 10 | 8 | 5 | 4 | 4 | 4 | 4 | 2 | 2 | 2 | 0 |
| 8 | 10 | 10 | 8 | 8 | 7 | 6 | 5 | 4 | 3 | 3 | 0 |

TABLE 9

No. of live mussels in each pot over time (1.15 g KCl)

| Time (hrs) | C1 0.5 | C2 1 | C3 1.5 | C4 2 | C5 3 | C6 3.5 | C7 4.5 | C8 5 | C9 6 | C10 7.5 | C11 9 | C12 11.5 | C13 24 |
|---|---|---|---|---|---|---|---|---|---|---|---|---|---|
| 1 | 10 | 10 | 9 | 9 | 8 | 7 | 7 | 6 | 6 | 3 | 3 | 3 | 0 |
| 4 | 10 | 10 | 10 | 9 | 9 | 8 | 8 | 7 | 7 | 5 | 4 | 4 | 0 |
| 3 | 10 | 9 | 9 | 7 | 7 | 6 | 6 | 4 | 4 | 3 | 3 | 3 | 0 |
| 4 | 10 | 10 | 10 | 10 | 10 | 9 | 9 | 8 | 7 | 6 | 3 | 3 | 0 |
| 5 | 10 | 10 | 10 | 10 | 9 | 9 | 8 | 7 | 6 | 6 | 5 | 5 | 0 |
| 6 | 10 | 9 | 9 | 9 | 8 | 8 | 7 | 6 | 4 | 4 | 3 | 3 | 1 |
| 7 | 10 | 10 | 10 | 9 | 9 | 7 | 5 | 4 | 4 | 3 | 2 | 2 | 0 |
| 8 | 10 | 10 | 10 | 10 | 9 | 9 | 7 | 5 | 5 | 3 | 2 | 2 | 1 |

As can be seen in FIG. 9 (mean numbers of mussels alive per beaker at intervals in the first 24 hours following the five different treatments) with 0.5 g and 0.05 g of Batch 7 and with only Palmitic acid added, there is no mortality within the first 24 hours (although there is a little mortality with both concentrations of Batch 7 over the next two days. Both 5 g of Batch 7 and 1.15 g of KCl cause rapid mortality, especially over the first 8 hours. Batch 7 seems to be the most rapidly acting of these two treatments, even though both contain the same quantity of salt.

FIG. 10 (the mean lengths of remaining mussels at intervals after addition of treatment 1) shows that with treatment 1 there are significant differences in the sizes of mussels that die at various times in the experiment (1-way anova, df=9, p=0.05).

Figure 3:
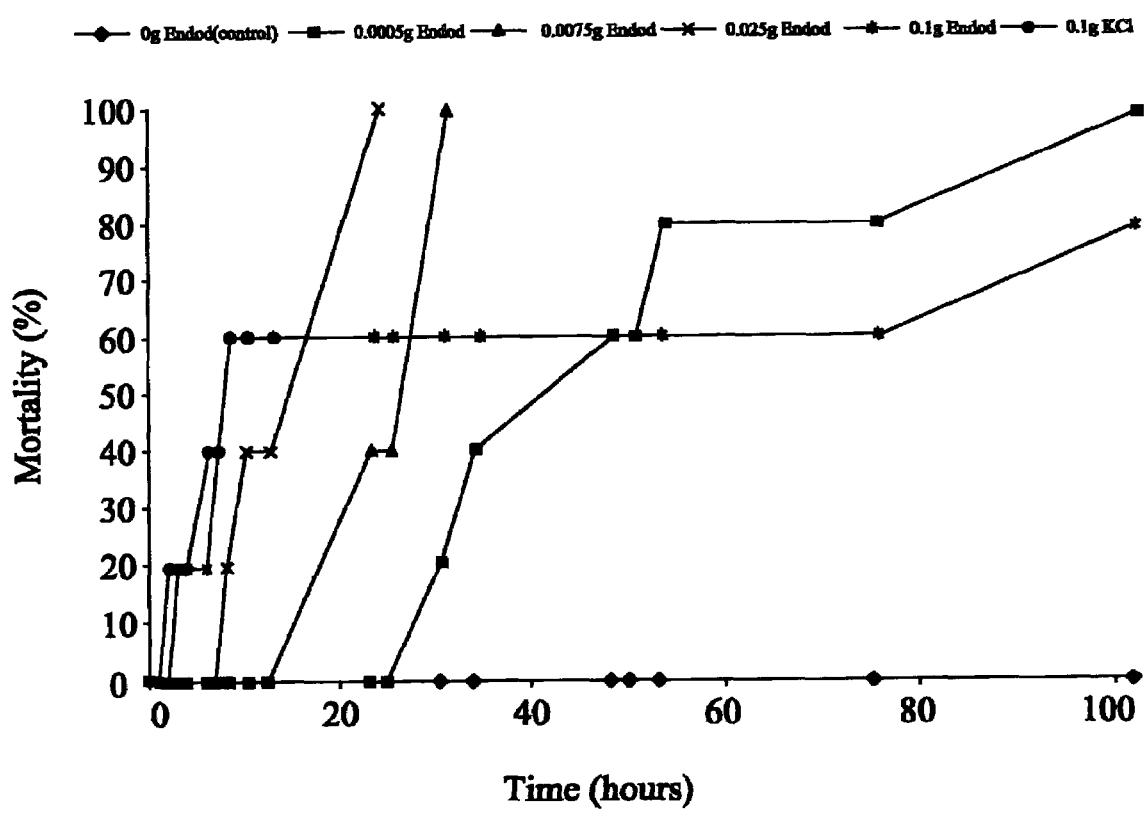
FIG. 3 illustrates the results shown in table 2 in the form of a graph.
Figure 2A:
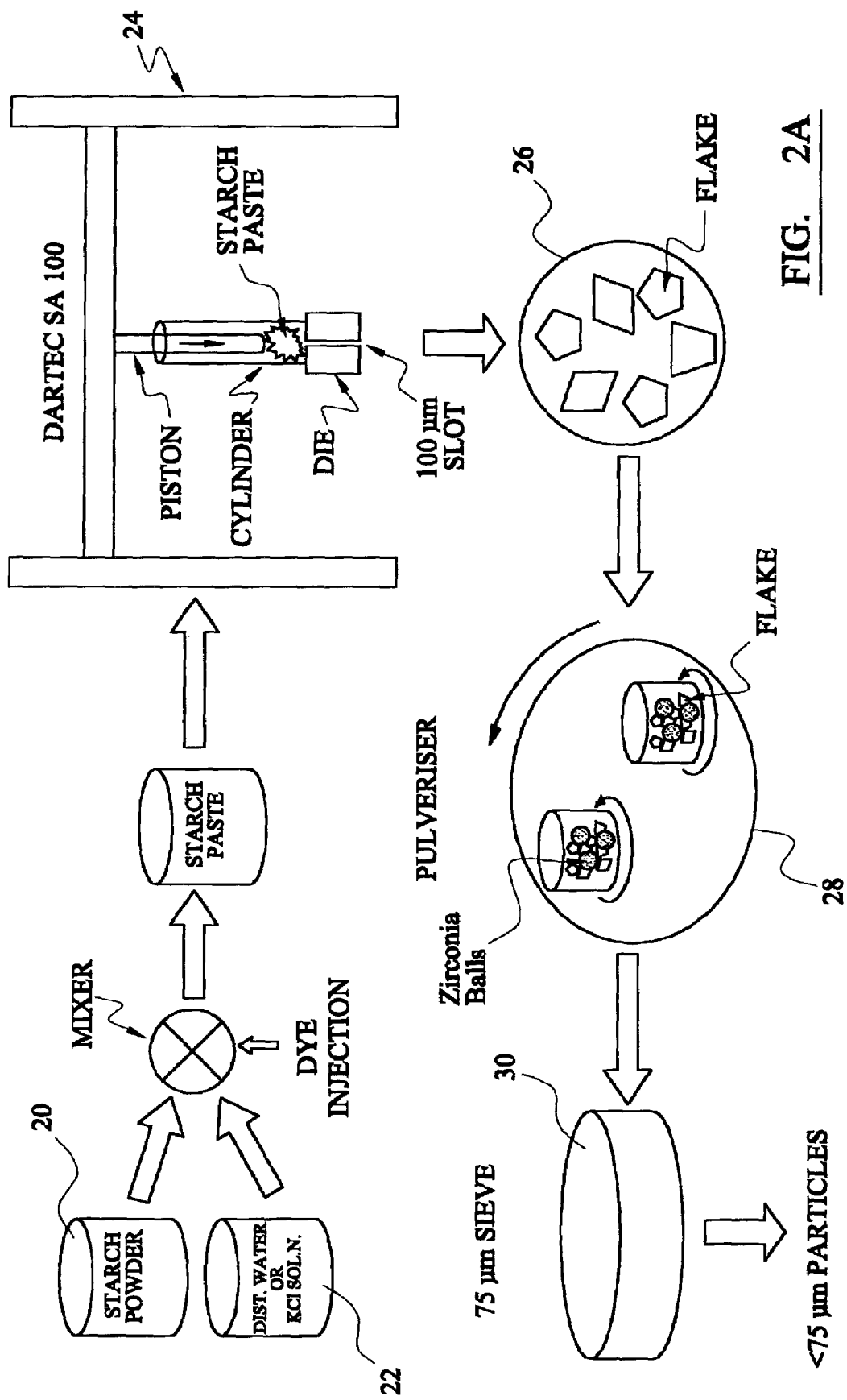
FIG. 2a illustrates a method of producing particles with a starch-based carrier material.

Mean sizes of the fatalities and survivors with addition of treatments 2 and 3 were then compared. FIG. 3 summarises the results with the two treatments pooled. The mean size of the survivors is significantly smaller than that of those that died (two sample t-test, df=158, p=0.0001).

Figure 12:
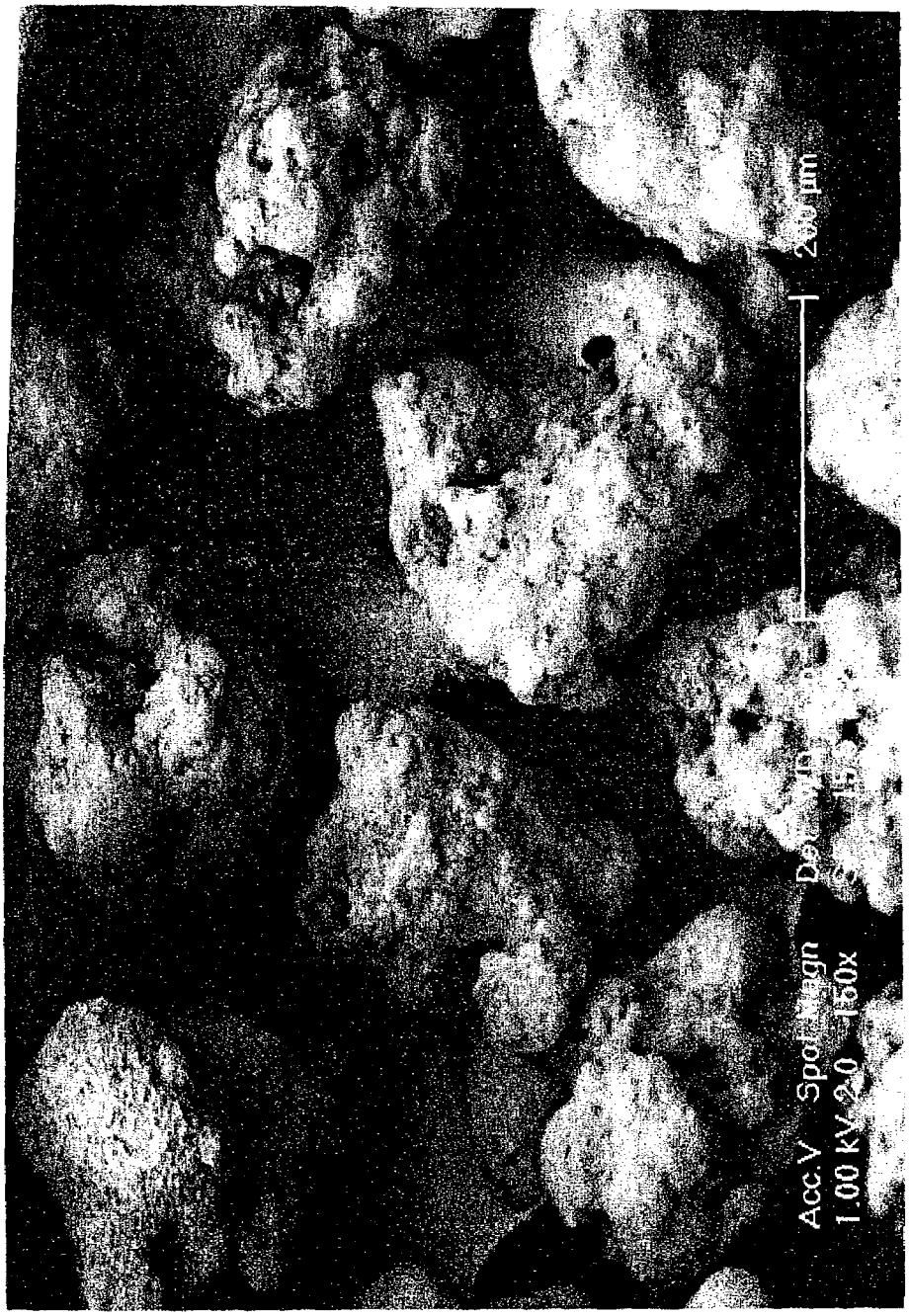
Figure 13:
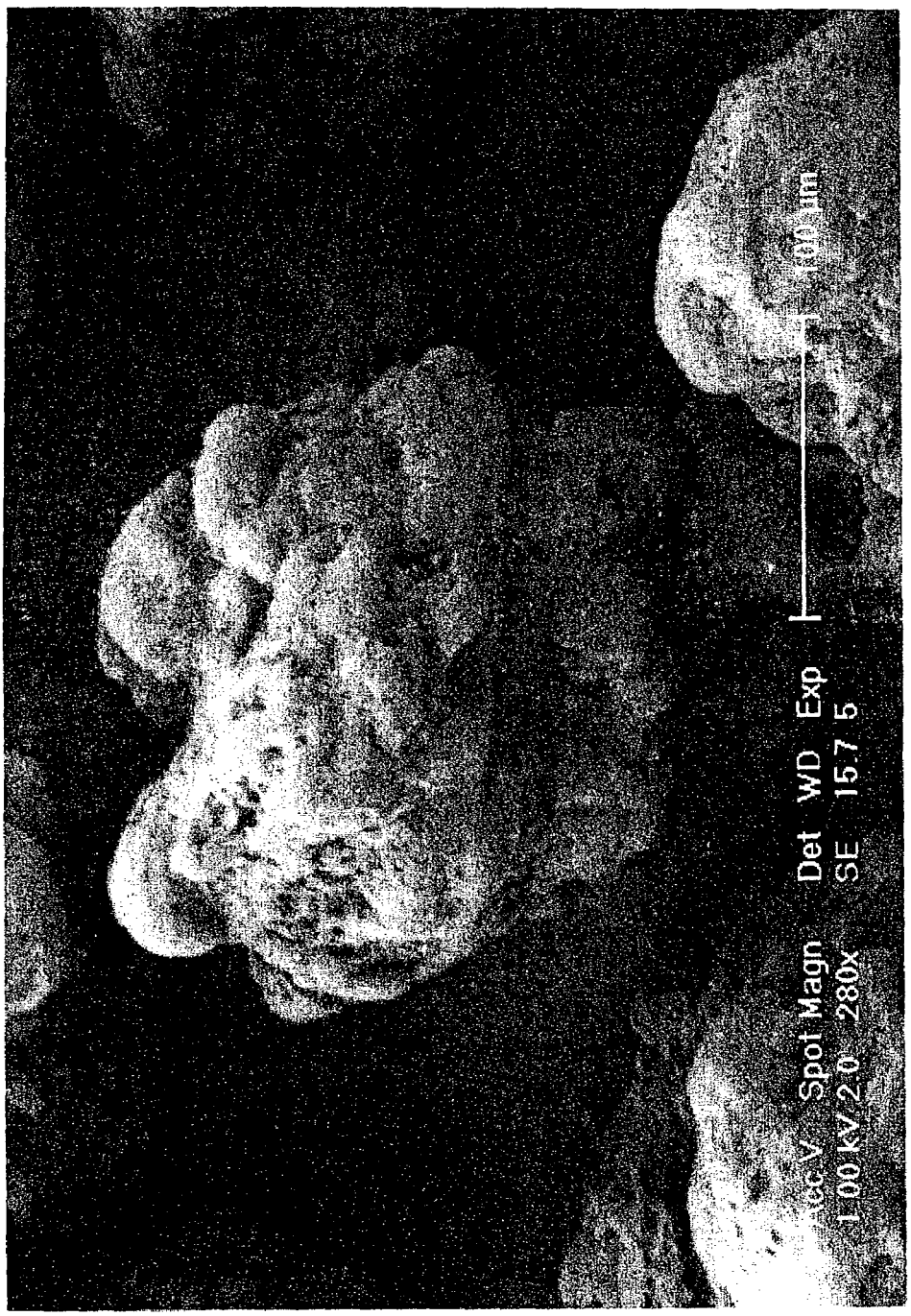

FIGS. 12 and 13 are scanning electron micrographs (SEMs) of particles comprising 90 micron potassium permanganate coated in palmitic acid, the particles being manufactured by fluidised bed spray congealing. The particles shown are in the size range 150 to 250 microns (as determined by size fractioning by sieving).

Figure 14:
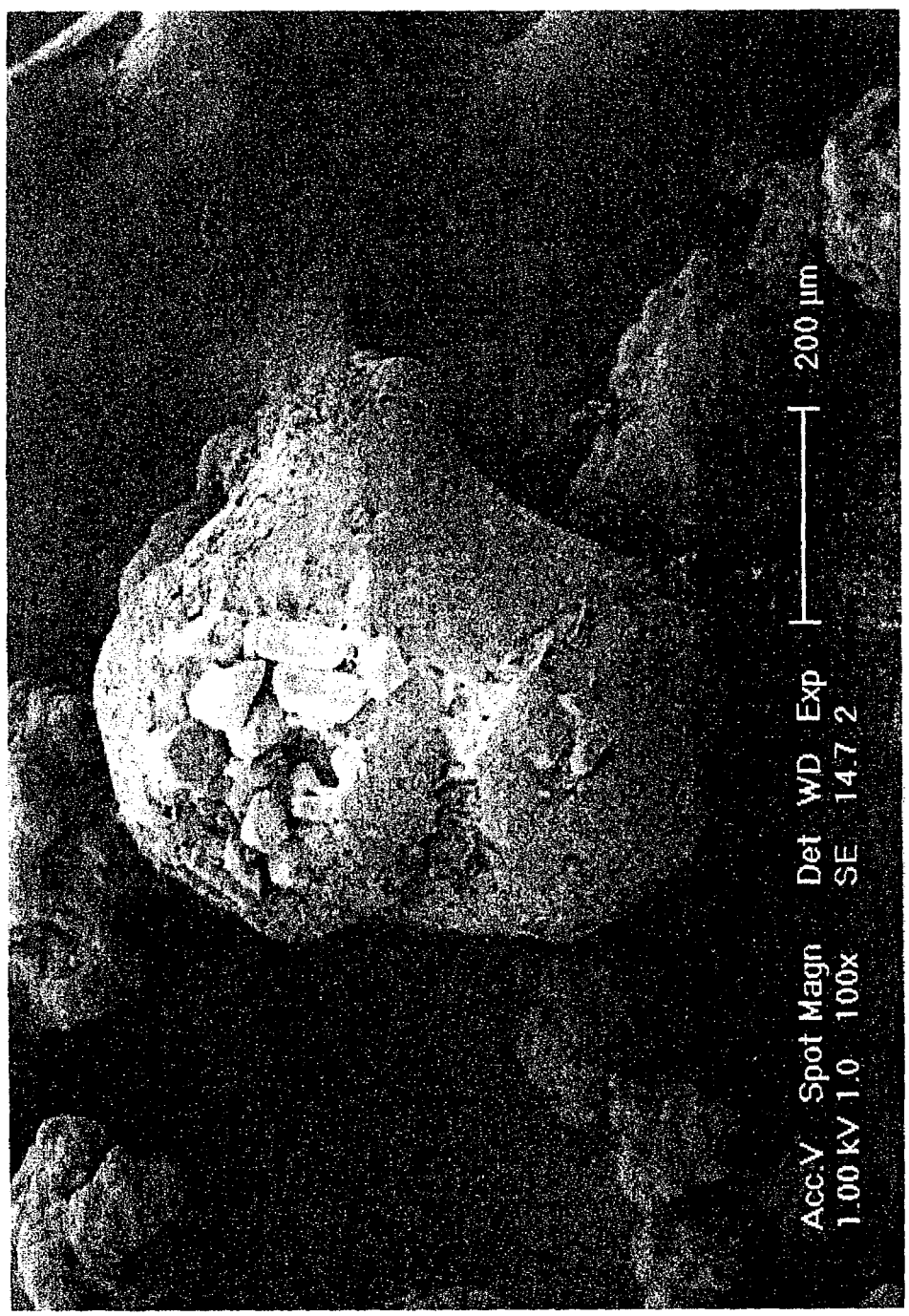
Figure 15:
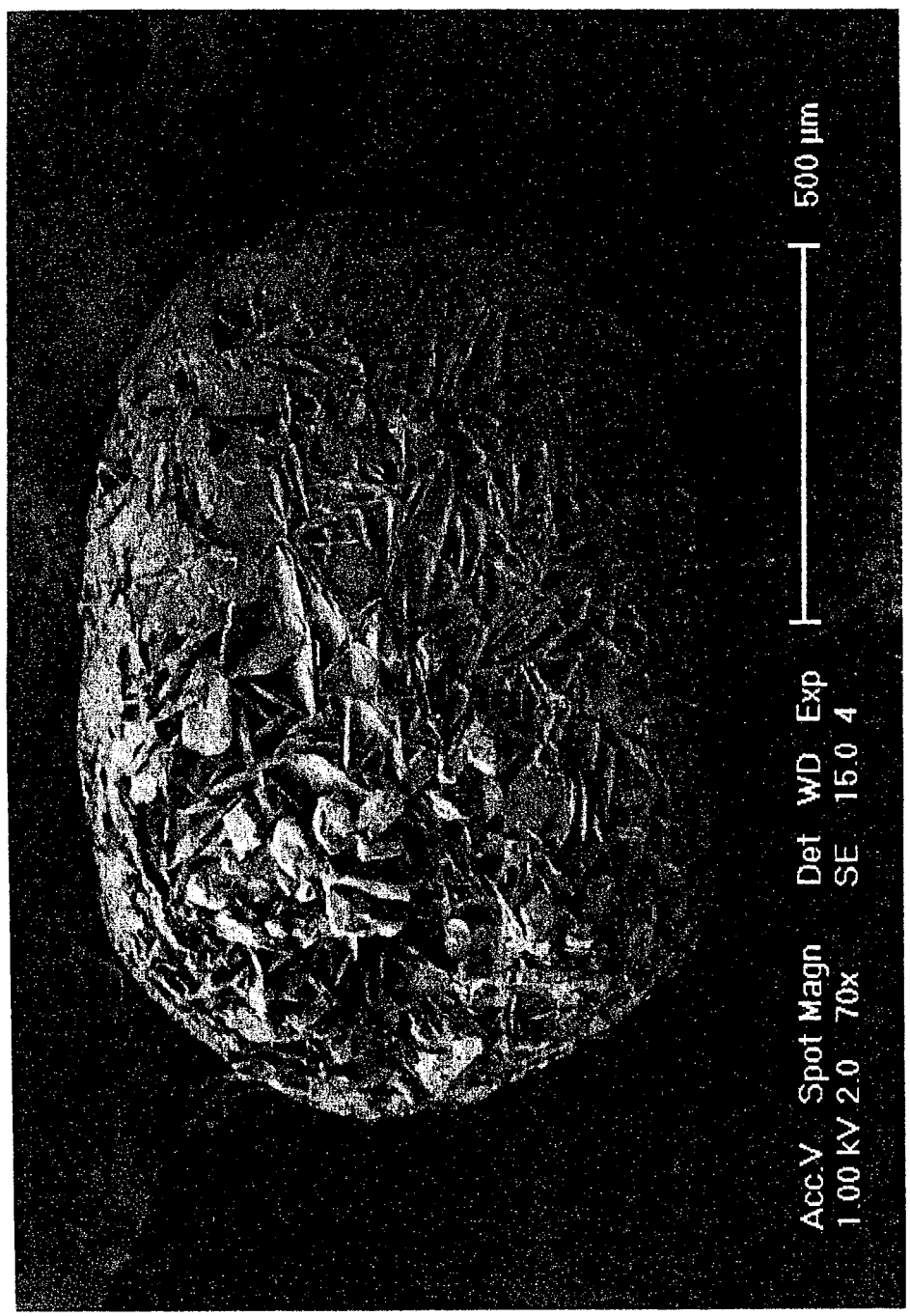

FIGS. 14 and 15 are SEMs of similar particles but of a size greater than 250 microns.

Figure 16:
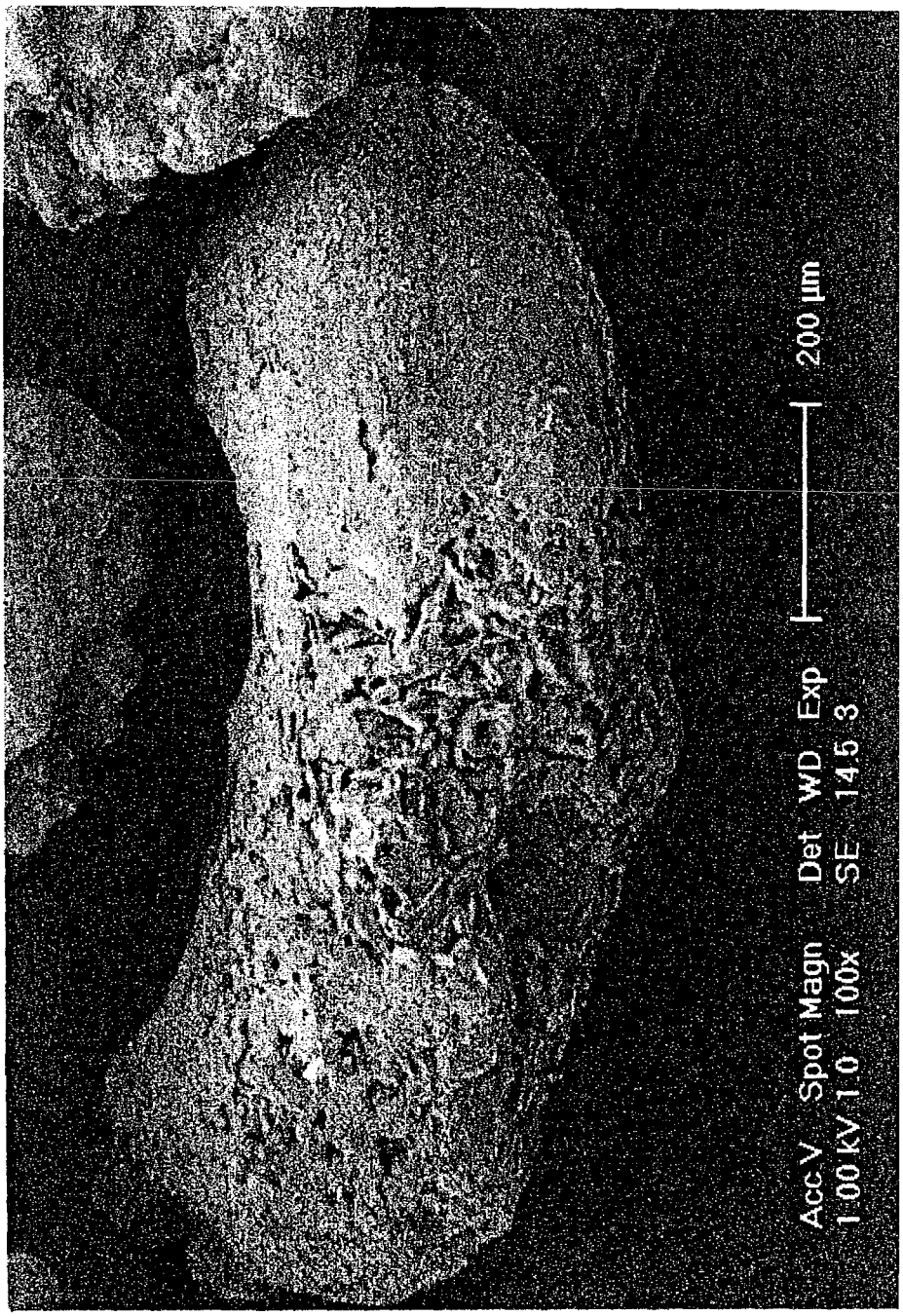

FIG. 16 is a SEM of particles of a size greater than 250 microns comprising 98 micron potassium chloride coated in palmitic acid, manufactured by fluidised bed spray congealing.

FIG. 17 comprises a series of photomicrographs of particles from two different samples indicated by (7) and (9), during size fractionation by sieving (the numbers 90, 150, 250 indicates the size in microns of sieve the sample was retained on whereas Res indicates that the sample passed through a 90 micron sieve). The bars shown are equal to 400 μm. Sample (7) is the same sample as used in Experiment 8 whereas sample (9) comprises 43 μm potassium chloride particles to which 4 g of silica was added before spraying with stearic acid for 30 minutes.

The reader's attention is directed to all papers and documents which are filed concurrently with or previous to this specification in connection with this application and which are open to public inspection with this specification, and the contents of all such papers and documents are incorporated herein by reference.

All of the features disclosed in this specification (including any accompanying claims, abstract and drawings), and/or all of the steps of any method or process so disclosed, may be combined in any combination, except combinations where at least some of such features and/or steps are mutually exclusive.

Each feature disclosed in this specification (including any accompanying claims, abstract and drawings), may be replaced by alternative features serving the same, equivalent or similar purpose, unless expressly stated otherwise. Thus, unless expressly stated otherwise, each feature disclosed is one example only of a generic series of equivalent or similar features.

The invention is not restricted to the details of the foregoing embodiment(s). The invention extends to any novel one, or any novel combination, of the features disclosed in this specification (including any accompanying claims, abstract and drawings), or to any novel one, or any novel combination, of the steps of any method or process so disclosed.

The invention claimed is:

1. A method of controlling a population of aquatic filter feeding organisms comprising the steps of:
   i) introducing into the aquatic filter feeding organism's environment particles which are compatible with the selective feeding mechanism of aquatic filter feeding organisms, said particles including at least one substance that is toxic to the organism;
   ii) inducing the aquatic filter feeding organism to ingest the substance, by virtue of the substance being coated with or encapsulated within a slightly water soluble carrier material, which carrier material is innocuous and/or nutritious for and/or attractive to the aquatic filter feeding organism, thereby causing accumulation of the substance to a biologically active concentration within the aquatic filter feeding organism,
   wherein the substance is provided as a core surrounded by a coating of said carrier material; and
   wherein said core is between 40 and 60 microns in diameter and the coating is between 5 and 40 microns wherein the aquatic filter feeding organism is a mollusk.

2. A method according to claim 1, wherein the particles have neutral buoyancy in freshwater.

3. A method according to claim 1, wherein the method includes the step of contacting the filter feeder with the particles for at least 4 hours.

4. A method according to claim 1, wherein the organism is selected from the group consisting of mussels, clams and oysters.

5. A method according to claim 1 wherein the organism comprises Zebra mussels (Dreissena polymorpha).

6. A method according to claim 1, wherein the particles have a mean particle size in the range 1 to 200 microns in diameter.

7. A method according to claim 1, wherein the active ingredient is provided as a core of the particles surrounded by a coating of innocuous and/or nutritious and/or attractive carrier material around said core.

8. A method according to claim 1, wherein the particles are manufactured using complex coacervation, fluidised bed spray coating, or spray congealing techniques.

9. A method according to claim 1, wherein the active ingredient is potassium chloride or potassium permanganate.

10. A method according to claim 1, wherein the active ingredient is a saponin.

11. A method according to claim 1, wherein the active ingredient is derived from Endod berries or is a synthesized form of the active ingredients of Endod berries.

12. A method according to claim 1, wherein the carrier material is selected from the group consisting of starch, chocolate, waxes, beeswax, fatty acids, oils, fats, and dried plankton.

13. A method according to claim 1, wherein the carrier material comprises one or more fatty acids.

14. A method according to claim 1, wherein the particles include a surfactant.

15. A method of controlling a population of aquatic filter feeding organisms comprising:
   i) introducing into the aquatic filter feeding organism's environment particles which are compatible with the selective feeding mechanism of aquatic filter feeding organisms, said particles comprising at least one substance that is toxic to the organism and a carrier; wherein addition of the substance alone to said environment causes the organism to cease feeding; and wherein the substance is potassium chloride or potassium permanganate;
   ii) inducing the aquatic filter feeding organism to continue to ingest the particles by coating said substance or encapsulating said substance within a slightly water soluble carrier material, which carrier material is characterized by at least one property selected from the group consisting of nutritious, innocuous, and attractive to the organisms,
   iii) said coating preventing cessation of feeding, and thereby increasing accumulation of the substance to a biologically toxic concentration within the aquatic filter feeding organism wherein the aquatic filter feeding organism is a mollusk.

16. A method according to claim 15, wherein the particles have neutral buoyancy in freshwater.

17. A method according to claim 15, wherein the organism is selected from the group consisting of mussels, clams and oysters.

18. A method according to claim 15 wherein the organism comprises Zebra mussels (Dreissena polymorpha).

19. A method according to claim 15, wherein the particles have a mean particle size in the range 1 to 200 microns in diameter.

20. A method according to claim 15, wherein the active ingredient is provided as a core of the particles surrounded by a coating of innocuous and/or nutritious and/or attractive carrier material around said core.

21. A method according to claim 15, wherein the particles are manufactured using complex coacervation, fluidized bed spray coating, or spray congealing techniques.

22. A method according to claim 15, wherein the core is between 40 and 60 microns in diameter and the coating is between 5 and 40 microns.

23. A method according to claim 15, wherein the method includes the step of contacting the filter feeder with the particles for at least 4 hours.

24. A method according to claim 15, wherein the carrier material is selected from the group consisting of starch, chocolate, waxes, beeswax, fatty acids, oils, fats, and dried plankton.

25. A method according to claim 15, wherein the carrier material comprises one or more fatty acids.

26. A method according to claim 15, wherein the particles include a surfactant.

* * * * *